(12) United States Patent
Hutchens et al.

(10) Patent No.: US 6,734,022 B2
(45) Date of Patent: *May 11, 2004

(54) METHOD AND APPARATUS FOR DESORPTION AND IONIZATION OF ANALYTES

(75) Inventors: T. William Hutchens, Los Altos, CA (US); Tai-Tung Yip, Cupertino, CA (US)

(73) Assignee: Baylor College of Medicine, Houston, TX (US)

( * ) Notice: Subject to any disclaimer, the term of this patent is extended or adjusted under 35 U.S.C. 154(b) by 50 days.

This patent is subject to a terminal disclaimer.

(21) Appl. No.: 09/809,657

(22) Filed: Mar. 15, 2001

(65) Prior Publication Data

US 2001/0014479 A1 Aug. 16, 2001

Related U.S. Application Data

(63) Continuation of application No. 08/068,896, filed on May 28, 1993, now abandoned.

(51) Int. Cl.$^7$ ............................................. G01N 33/537
(52) U.S. Cl. ....................... 436/173; 436/174; 436/178; 436/155; 250/287; 435/7.1; 536/25.4
(58) Field of Search ................................. 436/174, 173, 436/63, 178, 155; 250/287, 288; 435/7.1, 6; 536/25.4

(56) References Cited

U.S. PATENT DOCUMENTS

| | | |
|---|---|---|
| 3,896,661 A | 7/1975 | Parkhurst et al. |
| 4,022,876 A | 5/1977 | Anbar |
| 4,295,046 A | 10/1981 | Grüter et al. |
| 4,296,332 A | 10/1981 | Hill |
| 4,454,233 A | 6/1984 | Wang |
| 4,468,468 A | 8/1984 | Benninghoven et al. |
| 4,686,366 A | 8/1987 | Stuke |
| 4,694,167 A | 9/1987 | Payne et al. |
| 4,705,616 A | 11/1987 | Andresen et al. |
| 4,902,627 A | 2/1990 | Kidwell |
| 4,988,879 A | 1/1991 | Zare et al. |
| 5,003,059 A | 3/1991 | Brennan |
| 5,045,694 A | 9/1991 | Beavis et al. |
| 5,078,135 A | 1/1992 | Caprioli |
| 5,118,937 A | 6/1992 | Hillenkamp et al. |
| 5,124,267 A | 6/1992 | Humpel et al. |
| 5,171,989 A | 12/1992 | Williams et al. |
| 5,209,919 A | 5/1993 | Turteltaub et al. |
| 5,547,835 A | 8/1996 | Koster |
| 5,719,060 A * | 2/1998 | Hutchens et al. ........... 436/174 |
| 6,225,047 B1 | 5/2001 | Hutchens et al. |
| 6,579,719 B1 | 6/2003 | Hutchens et al. |

FOREIGN PATENT DOCUMENTS

| | | |
|---|---|---|
| EP | 00/84086 | 7/1983 |
| EP | 03/33912 | 9/1989 |
| GB | 22/35528 | 3/1991 |
| GB | 22/35529 | 3/1991 |
| WO | WO 91/02961 | 3/1991 |
| WO | WO 92/13629 | 8/1992 |
| WO | WO 96/3777 | 11/1996 |
| WO | WO 96/40888 | 12/1996 |

OTHER PUBLICATIONS

Karas, M. et al. Laser Desorption Ionization of Proteins with Molecular Masses Exceeding 10,000 Daltons, *Analytical Chemistry* 60:2299–2301 (1988).

Rivera, A. A Summary Statement: Probes for Affinity Mass Spectrometry of Phosphoproteins (Apr. 1994).

Nelson, et al. Mass Spectrometric Immunoassay, *Analytical Chemistry* 67:111–89–102 (1991).

Beavis, R. et al. Epitaxial Protein Inclusion in Sinapic Acid Crystals, *J. Phys. D: Appl. Phys.* 26:442–447 (1993).

Strupat, K. et al. 2,5–Dihydroxybenzoic Acid: A New Matrix for Laser Desorption–ionization Mass Spectrometry; Int'l Journal of Mass Spectrometry and Ion Processes, 111–89–102 (1991).

Karas, M. et al. UV–Laser Desorption/Ionization Mass Spectrometry of Femtomol Amounts of Large Proteins, *Biomedical & Environmental Mass Spectrometry* 18:841–843 (1989).

Nelson, et al. Mass Spec. Analysis of a Transition–metal–binding Peptide Using MALDTOFMS: A Demonstration of Probe Tip Chemistry, Rapid Communications in Mass Spec. 6:4–8 (1992).

Dwyer, J. et al., A Novel Sample Preparation Device for MALDI–MS, International Library 13A–13F (1997).

American Biotechnology Laboratory, Feb. 1994 cover, cover–p. 2 (1994).

Hillenkamp, F., Laser Desorption Mass Spectrometry: Mechanisms Techniques and Applications, Bordeaux Mass Spectometry Conference Report 11A:354–362 (1988).

(List continued on next page.)

*Primary Examiner*—Lyle A. Alexander
(74) *Attorney, Agent, or Firm*—Townsend & Townsend & Crew LLP

(57) ABSTRACT

This invention relates generally to methods and apparatus for desorption and ionization of analytes for the purpose of subsequent scientific analysis by such methods, for example, as mass spectrometry or biosensors. More specifically, this invention relates to the field of mass spectrometry, especially to the type of matrix-assisted laser desorption/ionization, time-of-flight mass spectrometry used to analyze macromolecules, such as proteins or biomolecules. Most specifically, this invention relates to the sample probe geometry, sample probe composition, and sample probe surface chemistries that enable the selective capture and desorption of analytes, including intact macromolecules, directly from the probe surface into the gas (vapor) phase without added chemical matrix.

20 Claims, 21 Drawing Sheets

OTHER PUBLICATIONS

Karas, M., Ultraviolet Laser Desorption of Proteins Up to 120,000 Daltons, Bordeaux Mass Spectrometry Conference Report 11A:416–417 (1988).

Hutchens, T.W. et al., Differences in the Confrontational State of a Zinc–finger DNA–binding Protein Domain Occupied by Zinc and Copper Revealed by Electrospray Ionization Mass Spectrometry, Rapid Communications in Mass Spec. 6:469–473 (1992).

Hutchens, T.W., et al., New Desorption Strategies for the Mass Spectrometric Analysis of Macromolecules, Rapid Communications in Mass Spec. 7:576–580 (1993).

Xiang, F., A Method to Increase Contaminant Tolerance in Protein Matrix–assisted Laser Desorption/Ionization by the Fabrication of Thin Protein–doped Polycrystalline Films, Rapid Communications in Mass Spec. 8:199–204 (1994).

Mock, K.K. et al., Sample Immobilization Protocols for Matrix–assisted Laser Desorption Mass Spectrometry, Rapid Communications in Mass Spec. 6:233–238 (1994).

Speir, J.P. et al. Substrate–assisted Laser Desorption of Neutral Peptide Molecules, Analytical Chemistry 64: 1041–1045 (1992).

Yip, T. et al, Protein Expression and Purification 2:355–362 (1991).

Van Breemen et al., Time—Resolved Laser Desorption Mass Spectrometry. I. Desorption of Performed Ions, Elsevie Scientific Publishing Company, International Journal of Mass Spectrometry and Ion Physics 49(1983): 36–51.

Jonsson, Gunnar P., et al., Plasma Desorption Mass Spectrometry of Peptides and Proteins Adsorbed on Nitrocellulose, Analytical Chemistry, 58:1084–1087 (1988).

* cited by examiner

METHOD AND APPARATUS FOR DESORPTION AND IONIZATION OF ANALYTES

This application is a Continuation of U.S. application Ser. No. 08/068,896 filed May 28, 1993, now abandoned the contents of which are incorporated herein by reference in its entirety.

This invention was made with government support under Grant No. 58-6250-1-003, awarded by the United States Department of Agriculture. The government may have certain rights.

BACKGROUND OF THE INVENTION

1. Field of the Invention

This invention relates generally to methods and apparatus for desorption and ionization of analytes for the purpose of subsequent scientific analysis by such methods, for example, as mass spectrometry or biosensors. More specifically, this invention relates to the field of mass spectrometry, especially to; the type of matrix-assisted laser desorption/ionization, time-of-flight mass spectrometry used to analyze macromolecules, such as proteins or biomolecules.

2. Description of the Prior Art

Generally, analysis by mass spectrometry involves the vaporization and ionization of a small sample of material, using a high energy source, such as a laser, including a laser beam. The material is vaporized from the surface of a probe tip by the laser beam, and in the process, some of the individual molecules are ionized by the gain of a proton. The positively charged ionized molecules are then accelerated through a short high voltage field and let fly into a high vacuum chamber, at the far end of which they strike a sensitive detector surface. Since the time of flight is a function of the mass of the ionized molecule, the elapsed time between ionization and impact can be used to determine the molecule's mass which, in turn, can be used to identify the presence or absence of known molecules of specific mass.

All known prior art procedures which present proteins or other large biomolecules on a probe tip for laser desorption/ionization time-of-flight mass spectrometry rely on a crystalline solid mixture of the protein or other analyte molecule in a large excess of acidic matrix material deposited on the bare surface of a metallic probe tip. (The sample probe tip typically is metallic, either stainless steel, nickel plated material or platinum). Immobilizing the analyte in such a matrix was thought to be necessary in order to prevent the destruction of analyte molecules by the laser beam. The laser beam strikes the mixture on the probe tip and its energy is used to vaporize a small portion of the matrix material along with some of the embedded analyte molecules. Without the matrix the analyte molecules are easily fragmented by the laser energy, so that the mass, and identity, of the original macromolecule is very difficult to determine.

This prior art procedure has several limitations which have prevented its adaptation to automated protein or other macrobiological molecules analysis. First, in a very crude sample it is necessary to partially fractionate (or otherwise purify the sample as much as possible) to eliminate the presence of excessive extraneous materials in the matrix/analyte crystalline mixture. The presence of large quantities of components may depress the signal of the targeted analyte. Such purification is time-consuming and expensive and would be very difficult to do in an automated analyzer.

Second, while the amount of analyte material needed for analysis by the prior art method is not large (typically in a picomole range), in some circumstances, such as tests on pediatric patients, analyte fluids are available only in extremely small volumes (microliters) and may be needed for performing several different analyses. Therefore, even the small amount needed for preparation of the analyte/matrix crystalline mixture for a single analysis may be significant. Also, only a tiny fraction (a few thousandths or less) of analyte used in preparing the analyte/matrix mixture for use on the probe tip is actually consumed in the mass spectrometry analysis. Any improvement in the prior art procedure which made it possible to use much less analyte to conduct the test would be highly advantageous in many clinical areas.

Third, the analyte protein, or other macromolecule, used in preparing the analyte matrix for use on the probe tip is not suitable for any subsequent chemical tests or procedures because it is bound up in the matrix material. Also, all of the matrix material used to date is strongly acidic, so that it would affect many chemical reactions which might be attempted on the mixture in order to modify the analyte molecules for subsequent examination. Any improvement in the procedure which made it possible to conduct subsequent chemical modifications or reactions on the analyte molecules, without removing them from the matrix or the probe tip, would be of enormous benefit to researchers and clinicians.

Additional limitations in the prior art included problems with matrix use such as:

(1) formation of analyte-matrix complex (referred to as "matrix adduct" which interferes with the accuracy of analyte measurement;

(2) inability to wash away contaminants present in analyte or matrix (e.g., other proteins or salts);

(3) formation of analyte-salt ion adducts;

(4) less than optimum solubility of analyte in matrix;

(5) signal (molecular ion) suppression "poisoning" due to simultaneous presence of multiple components; and (6) selective analyte desorption/ionization.

There are a number of problems and limitations with the prior art methods. Prior investigators, including Karas and Hillenkamp have reported a variety of techniques for analyte detection using mass spectroscopy, but these techniques suffered because of inherent limitations in sensitivity and selectivity of the techniques, specifically including limitations in detection of analytes in low volume, undifferentiated samples. The "Hillenkamp-Karas" articles that pertain to this field of invention are:

1. Hillenkamp, "Laser Desorption Mass Spectrometry: Mechanisms, Techniques and Applications"; *Bordeaux Mass Spectrometry Conference Report,* 1988, pages 354–362.

2. Karas and Hillenkamp, "Ultraviolet Laser Desorption of Proteins Up to 120,000 Daltons", *Bordeaux Mass Spectrometry Conference Report,* 1988, pages 416, 417.

3. Karas and Hillenkamp, "Laser Desorption Ionization of Proteins With Molecular Masses Exceeding 10,000 Daltons", *Anatical Chemistry,* 60. 2299, July 1988.

4. Karas, Ingendoh, Bahr and Hillenkamp, "UV-Laser Desorption/Ionization Mass Spectrometry of Femtomol Amounts of Large Proteins", *Biomed. Environ. Mass Spectrum* (in press).

The use of laser beams in time-of-flight mass spectrometers is shown, for example, in U.S. Pat. Nos. 4,694,167; 4,686,366, 4,295,046, and 5,045,694, incorporated by reference.

The first successful molecular mass measurements of intact peptides and small proteins (only up to about 15 kDa) by any form of mass spectrometry were made by bombarding surfaces with high energy particles (plasma desorption and fast atom bombardment mass spectrometry); this breakthrough came in 1981 and 1982. Improvements came in 1985 and 1986, however, yield (signal intensities), sensitivity, precision, and mass accuracy remained relatively low. Higher molecular mass proteins (about 20 to 25 kDa) were not observed except on rare occasions; proteins representing average molecular weights (approximately 70 kDa) were not ever observed with these methods. Thus, evaluation of most proteins by mass spectrometry remains unrealized.

In 1988, Hillenkamp and his coworkers used UV laser desorption time-of-flight mass spectrometry and discovered that when proteins of relatively high molecular mass were deposited on the probe tip in the presence of a very large molar excess of an acidic, UV absorbing chemical matrix (nicotinic acid) they could be desorbed in the intact state. This new technique is called matrix-assisted laser desorption/ionization (MALDI) time-of-flight mass spectrometry. Note that laser desorption time-of-flight mass spectrometry (without the chemical matrix) had been around for some time, however, there was little or no success determining the molecular weights of large intact biopolymers such as proteins and nucleic acids because they were fragmented (destroyed) upon desorption. Thus, prior to the introduction of a chemical matrix, laser desorption mass spectrometry was essentially useless for the detection of specific changes in the mass of intact macromolecules (see below). Note that the random formation of matrix crystals and the random inclusion of analyte molecules in the solid solution is prior art.

SUMMARY OF THE INVENTION

The primary object of the invention is to provide improved methods, materials composition and apparatus for coupled adsorption, desorption and ionization of multiple or selected analytes into the gas (vapor) phase, preferably for use in conjunction with mass spectrometry of biomolecules and other macromolecules, as well as by means of analytic detection other than mass spectrometry. The invention incudes a flexible variety of options for presenting surfaces with attached energy absorbing molecules, defined reaction sites, and affinity reagents for the capture,e transfer, and/or the desorption of analytes before and after a sseries of chemical, physical, and/or enzymatic modifications performed in situ.

Another object is to provide such a method and apparatus for affinity-directed detection of analytes, including desorption and ionization of analytes in which the analyte is not dispersed in a matrix solution or crystalline structure but is presented within, on or above an attached surface of energy absorbing "matrix" material through molecular recognition events, in a position where it is accessible and amenable to a wide variety of chemical, physical and biological modification or recognition reactions.

The probe surface with and without bonded energy absorbing molecules, referred to as the sample presenting surface can be composed of a variety of materials, including porous or nonporous materials, with the porous materials providing sponge-like, polymeric, high surface areas for optimized adsorption and presentation of analyte.

These surface materials can be substituted (at varying densities) with chemically bonded (covalent or noncovalent) affinity adsorption reagents and/or chemically bonded (i.e., immobilized) energy absorbing molecules (bound "matrix" molecules). The geometry of the sample presenting surface can be varied (i.e., size, texture, flexibility, thickness, etc.) to suit the need (e.g., insertion into a living organism through spaces of predetermined sizes) of the experiment (assay).

Another object is to provide such a method and apparatus in which the analyte material is chemically bound or physically adhered to a substrate forming a probe tip or other sample presenting surface.

A further object is to, provide means for the modification of probe or sample presenting surfaces with energy-absorbing molecules to enable the successful desorption of analyte molecules without the addition of exogenous matrix molecules as in prior art.

A further object is to provide the appropriate density of energy-absorbing molecules bonded (covalently or noncovalently) in a variety of geometries such that mono layers and multiple layers of attached energy-absorbing molecules can be used to facilitate the desorption of analyte molecules of varying masses. The optimum ratio of adsorbed or bonded energy-absorbing molecules to analyte varies with the mass of the analyte to be detected. A further object is to modify the sample presenting surface with such energy-absorbing molecules where the composition of the probe or sample presenting surface is other than the metal or metallic surfaces as described in prior art. Separate from the chemical and/or physical modification of the probe surface with energy absorbing molecules is the modification of these surfaces with affinity reagents, both chemical and/or biological, for the specific purpose of capturing (adsorbing) specific analyte molecules or classes of analyte molecules for the subsequent preparation, modification, and successful desorption of said analyte molecules.

A further object is to provide all combinations of surfaces modified with energy-absorbing molecules and/or affinity-directed analyte capture devices to enable the selective and/or nonselective adsorption of analytes and the subsequent desorption either with or without requiring the subsequent addition of additional matrix molecules. It is important to note that the surfaces modified with affinity reagents for the capture of analytes are more useful than the underivitized sample surfaces described in prior art even when the deposition of energy-absorbing molecules (that is matrix) is as described in prior art. Because of the advantages in the ability to remove contaminating substances from the adsorbed analyte molecules and because of the ability to modify adsorbed analyte molecules without (or before) added matrix.

A further object is to provide such a method and apparatus in which the substrate forming the probe tip or other sample presenting surface is derivatized with one or more affinity reagents (a variety of densities and degrees of amplification) for selective bonding with predetermined analytes or classes of analytes.

A further object is to provide methods and apparatus for using probe tips having surfaces derivatized with affinity reagents and containing laser desorption matrix material (chemically bonded to surface or not) which may be used to isolate target analyte materials from undifferentiated biological samples such as blood, tears, urine, saliva, gastrointestinal fluids, spinal fluid, amniotic fluid, bone marrow, bacteria, viruses, cells in culture, biopsy tissue, plant tissue or fluids, insect tissue or fluids, etc.

Because of the new and preferred method for presentation and desorption of selected analytes, a further object is to use analyte detection methods other than the generic electron multipliers typically used in mass spectrometric devices. This would include but would not be limited to detection films/plates for the qualitative or quantitative evaluation of fluorescent or radio-labeled analytes or analyte molecule complexes.

A further object is to provide such a system in which the affinity reagent chemically bonds or biologically adheres to the target analyte or class of analytes.

A further object is to use existing and new solid phase affinity reagents (e.g., small diameter porous or nonporous beads of crosslineated polymer with attached molecular capture devices) designed for the (1) capture (adsorption of one or more analytes, (2) the preparation of these captured analytes (e.g., washing with $H_2O$ or other buffered or nonbuffered solutions to remove contaminants such as salts, multiple cycles of washing, such as with polar organic solvent, detergent-dissolving solvent, dilute acid, dilute base or urea), and (3) most importantly, the direct transfer of these captured and prepared analytes to the probe surface for subsequent analyte desorption (for detection, quantification and/or mass analysis).

A further object is to provide such a system in which the predetermined analytes are individual biomolecules or other macromolecules or combinations of adjoined molecules (i.e., complexes).

A still further object is to provide such a method and apparatus in which the matrix materials used are not strongly acidic, as in prior art matrices, but are chemically modified into the slightly acidic, neutral pH or strongly basic range of pH.

A further object is to provide such a system in which the matrix material has a pH above 6.0.

A still further object is to provide a method and apparatus for desorption and ionization of analytes in which unused portion of the analytes contained on the presenting surface remain chemically accessible, so that a series of chemical and/or enzymatic or other treatments (e.g., discovery of analyte-associated molecules by molecular recognition) of the analyte may be conducted on the probe tip or other presenting surface, in situ, followed by sequential analyses of the modified analyte by mass spectrometry. In one case (i.e., repetitive sequential analyses) the analyte is adsorbed to the sample presenting surface and can be treated (modified in situ after the excess free matrix is removed (i.e., washed away). Matrix can be added back before analysis by mass spectrometry. Using this procedure, an analyte can be repeatedly tested for a variety of components by removing one matrix, modifying the analyte sample, re-applying the same or different matrix, analyzing the sample, etc.

A further object is to provide a method and apparatus for the combined chemical and/or enzymatic modifications of target analytes for the purpose of elucidating primary, secondary, tertiary, or quaternary structure of the analyte and its components.

A still further object is to provide such a method and apparatus in which the probe tips or other sample presenting surfaces are; formed of a variety of materials, including electrically insulating materials (porous and nonporous), flexible or nonrigid materials, optically transparent materials (e.g., glass, including glass of varying densities, thicknesses, colors and with varying refractive indices), as well as less reactive, more biocompatible materials (e.g., biopolymers such as agarose, dextran, cellulose, starches, peptides, and fragments of proteins and of nucleic acids such as DNA (deoxyribonucleic acid) and RNA (ribonucleic acid). These surfaces can be chemically modified by the attachment of energy-absorbing molecules and/or affinity directed analyte capture molecules.

Another object is to provide a method and apparatus for desorption and ionization of analyte materials in which cations other than protons ($H^+$) are utilized for ionization of analyte macromolecules.

Note that the laser or light source used to convey energy to the probe surface can employ a wavelength(s) that is(are) not fixed but can be varied according to the wavelength absorbed by the matrix (whether the matrix is added in the free form or is chemically bonded to the probe (sample presenting) surface). For this procedure, a variety of wavelengths (10 or more) defined by absorbance of matrix or energy absorbing surface can be utilized.

Another object is to provide such a method and apparatus in which the probe tips or other sample presenting surfaces used for laser desorption/ionization time-of-flight mass spectrometry are magnetized and in which the matrix, affinity directed absorption molecules and/or analyte materials are magnetically adhered to such magnetized surface.

A further object is a method and apparatus in which the matrix and/or analyte materials are adhered by any variety of chemical mechanisms to the sample presenting surface.

A further objective is to provide energy-absorbing molecules which have been incorporated into other chemical structures (e.g., chemical or biological polymers) for the deposition (covalent or noncovalent) onto the sample presenting surface in a way that enables repetitious analyte desorption events without interference with chemical and/or enzymatic modifications of the analyte molecule(s) performed in situ.

Another object is to provide sample presenting surfaces in a variety of sizes and configurations (up to 4"×4") with multiple (up to 10,000 or more) spots (including spots down to <0.001 inch diameter) of affinity reagents arranged in predetermined arrays for the selective adsorption of numerous different analytes (e.g., clinical chemical marker proteins) to enable a wide spectrum sampling of the macromolecular composition of biological samples/fluids.

As shown more fully below, the present invention overcomes limitations and disabilities of the prior art by providing probe tips or sample plates whose surfaces have been derivatized with biospecific affinity reagents which will selectively bind specific groups or types of biomolecules or other analytes out of an undifferentiated sample (such as blood or urine). Appropriate selection of the affinity reagents used to derivatize the probe tip surface therefore makes possible the selection from the undifferentiated sample and binding to the probe tip of the specific types or groups of biological or other macromolecules under investigation, or subsequent examination (e.g., quantification and/or structure elucidation) by mass spectrometry. This has the advantage of achieving both the purification of the analyte sample previously required and the effect of concentrating the analyte. It reduces by a factor of 1,000 to 100,000 the amount of analyte needed for the mass spectrometry examination, since only the macromolecules which attach to the biospecific affinity reagents are removed from the analyte sample, and these can be sequestered on predetermined areas of the probe tips or sample plates that are even less than the laser spot size.

It also has been found that the probe tips used in the process of the invention need not be metal or metal-coated, as with prior art procedures. Research involved in the invention has involved glass and synthetic polymer surfaces such as polystyrene, polypropylene, polyethylene, polycarbonate and other polymers including biopolymers, for the probe tips which hate been covalently or noncovalently derivatized for immobilization of specific reagents that will direct the selective adsorption of specific analytes. These surfaces will include immobilized metal ions, immobilized proteins, peptides, enzymes, and inhibitor molecules, immobilized DNA and RNA, immobilized antibodies, immobilized reducing agents, immobilized carbohydrates and lectins, immobilized dyes and immobilized protein surface domains involved in molecular recognition (e.g., dimerization domains and subunits). Some of the chemical and surface structures are as yet unknown.

The preferred probe tip, or sample plate, for selective adsorption/presentation of sample for mass analysis are (1) stainless steel (or other metal) with a synthetic polymer coating (e.g., cross-linked dextran or agarose, nylon, polyethylene, polystyrene) suitable for covalent attachment of specific biomolecules or other nonbiological affinity reagents, (2) glass or ceramic, and/or (3) plastic (synthetic polymer). The chemical structures involved in the selective immobilization of affinity reagents to these probe surfaces will encompass the known variety of oxygen-dependent, carbon-dependent, sulfur-dependent, and/or nitrogen-dependent means of covalent or noncovalent immobilization. The methods and chemical reactions used in producing such surfaces derivatized with biospecific affinity reagents already are known by those skilled in the art. Two features of the invention, however, are (1) the specific size and localization of the derivatized surface with respect to the laser beam and (2) the affinity directed presentation of specific analyte molecules (e.g., macromolecule or biopolymer) at a defined surface density or local concentration required for the efficient detection by laser desorption/ionization time-of-flight mass spectrometry. This can be accomplished by arranging the affinity adsorption "spots" (0.005 to 0.080 inch diameter) on the probe surface in a defined manner (400 to 1,000 spots could be placed on a surface about the size of a glass slide).

An additional discovery involves the fact that pH modified chemical matrices can be used on these surfaces to facilitate desorption/ionization without disruption of conditions necessary for subsequent sample modification. As discussed above, prior art matrix materials used for biomolecular mass spectrometry are acidic. The exact chemical structure of the pH-modified matrices still are unknown. However, by suitable neutralization of the matrix material, it can be made largely passive to subsequent chemical or enzymatic reactions carried out on the analyte molecules presented on the derivatized probe tip surface by the biospecific affinity reagents. This makes possible the carrying out of chemical reactions on the analyte molecules presented on the probe tips. Since only a small fraction of the analyte molecules are used in each desorption/mass spectrometer measurement, a number of sequential chemical and/or enzymatic modifications of the samples, in situ, on the probe tips, and subsequent analysis of the modified samples by mass spectrometry, can be carried out on the same probe tips in order to more accurately determine exactly what molecule is present, or other characteristics or information about the molecule, including its structure.

Finally, even when these matrix molecules are immobilized on a probe tip surface, the analyte deposited on such a surface can be desorbed with a laser beam. This circumvents the contamination of the analyte by the matrix molecules. As a particular feature of the invention, we have shown that some energy absorbing molecules that do not work as "matrix" molecules when added to analytes as a solution of free molecules (as in prior art) do indeed work well to facilitate the desorption of intact analyte molecules after being immobilized.

It seems likely that these improvements in the procedure will enable bioanalytical and medical instrument manufacturers to develop a machine for the automated evaluation of a single protein sample deposited on a surface and modified with numerous chemical and/or enzymatic reactions performed in situ.

BRIEF DESCRIPTION OF THE DRAWINGS

The foregoing and other objects and advantages of the invention will be apparent from the following specification and from the accompanying drawings.

FIG. 8 (top) is a mass spectrum of human lactoferrin and rabbit anti-human lactoferrin IgG complex affinity adsorbed on paramagmetic Dynabead-sheep anti-rabbit IgG.

FIG. 18B is a mass spectrum of the same peptide mixtures on surface bound MAP-dihydroxybenzoic acid.

DESCRIPTION OF THE PREFERRED EMBODIMENTS DETAILED DESCRIPTION

Usage of Conventional Matrix in Aqueous, pH-neutralized Form

EXAMPLES

Figure 1:
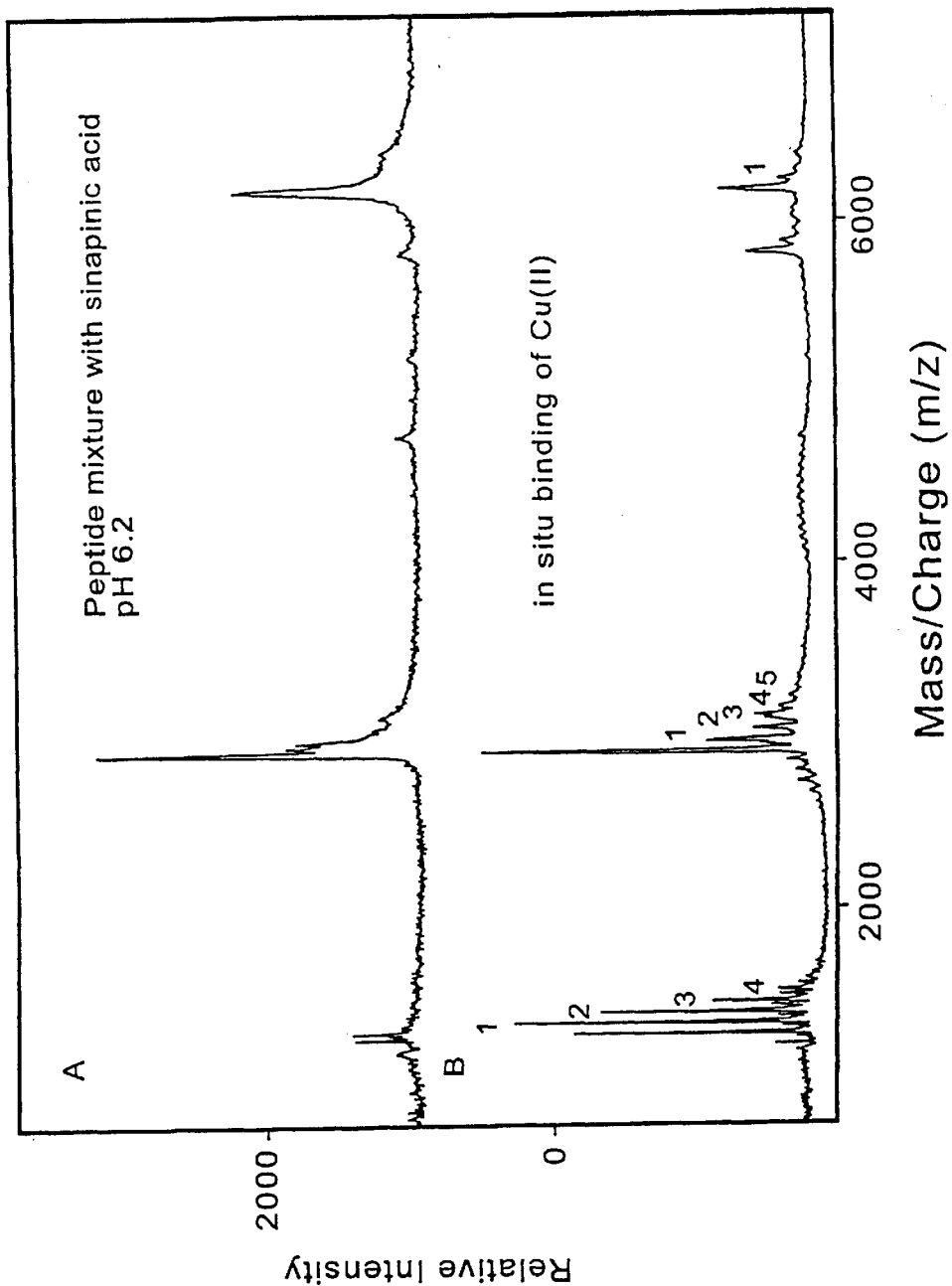
FIG. 1A is a mass spectrum of peptide mixtures using sinapinic acid pH 6.5 as the matrix.
FIG. 1B is a mass spectrum of the same peptide mixtures after in situ addition of $CuSO_4$.

Sinapinic acid (dimethoxy hydroxycinnamic acid) (Aldrich Chemical Co., Inc., Milwaukee, Wis.) 20 mg/ml water suspension (intrinsic pH 3.88) Dihydoxybenzoic acid (Aldrich) 20 mg/ml water (intrinsic pH 2.07) Cyanohydroxyinnamic acid (Aldrich) 20 mg/ml water suspension (intrinsic pH 3.3) each titrated with triethylamine (Pierce, Rockford, Ill.) to pH 6.5, 7.2 and 6.5 respectively 2 ul of the matrix solution was mixed with 1 ul of sample and allowed to air dry 1. A mixture of synthetic peptides—human histidine-rich glycoprotein peptide (GHHPH)$_2$G, (GHHPH)$_5$G, human estrogen receptor dimerization domain (D473-L525) with neutralized sinapinic acid as the matrix, in the absence and presence of Cu(II). FIG. 1 showed the in situ metal-binding properties of the peptides under neutralized condition.

Figure 2:
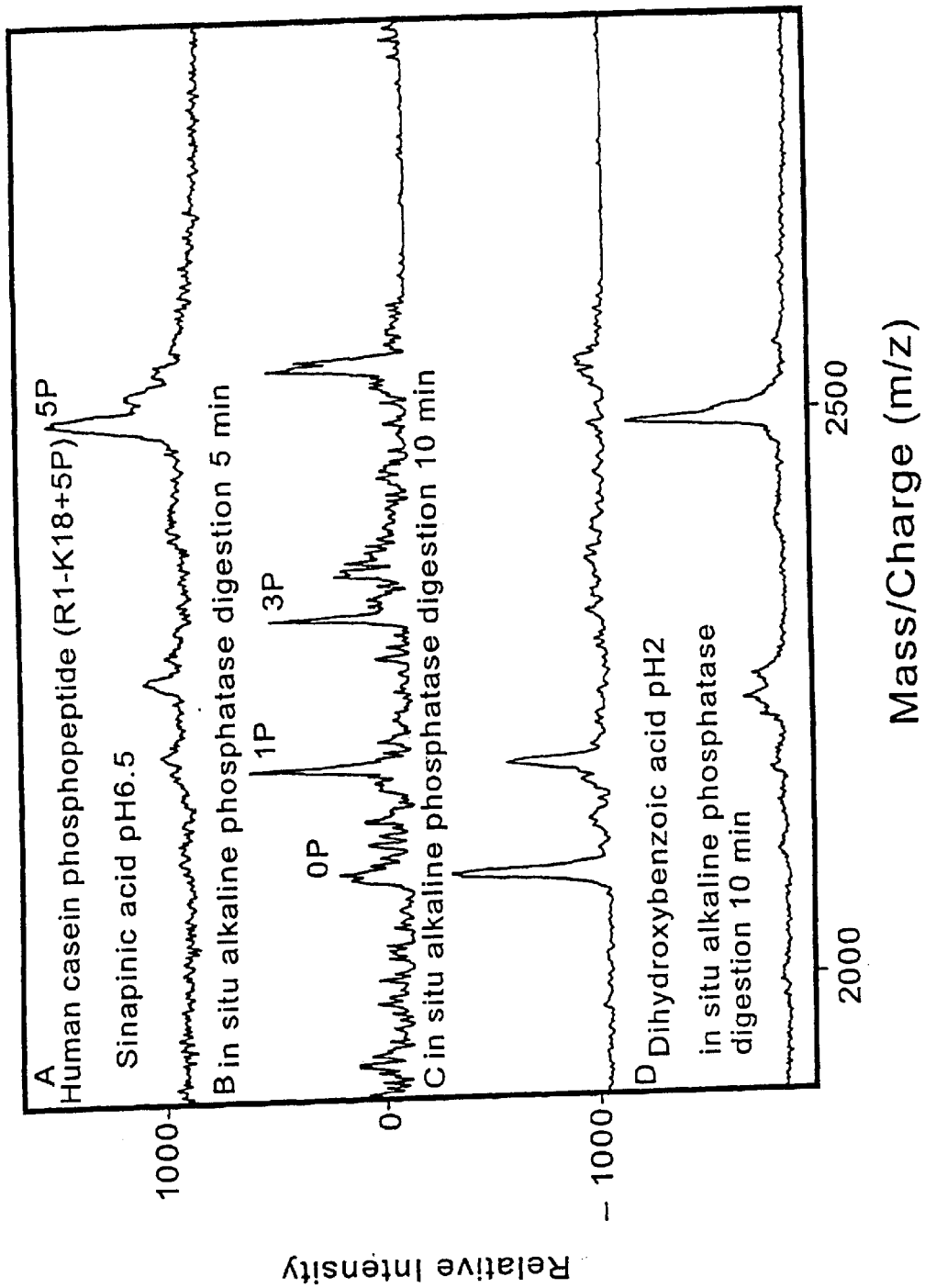
FIG. 2A is a mass spectrum of human casein phosphopeptide (R1-K18+5P) using sinapinic acid pH 6.5 as the matrix.
FIGS. 2B and 2C show the mass spectrum of the same peptide after in situ alkaline phosphatase digestion for 5 and 10 min respectively.
FIG. 2D shows the mass spectrum of the same peptide using dihydroxybenzoic acid pH 2 as the matrix, after in situ alkaline phosphatase digestion for 10 min.

2. Casein phosphopeptide (R1-K18+5P) with sinapinic acid pH 6.5. Followed by in situ alkaline phosphatase (0.5 ul, Sigma) digestion for 10 min at room temperature. Similar in situ digestion on the same pep tide with dihydoxybenzoic acid (prepared in 30% methanol/0.1% trifluoroacetic acid) was used as control. FIG. 2 showed the more efficient enzymatic dephosphorylation under neutralized condition.

Figure 3:
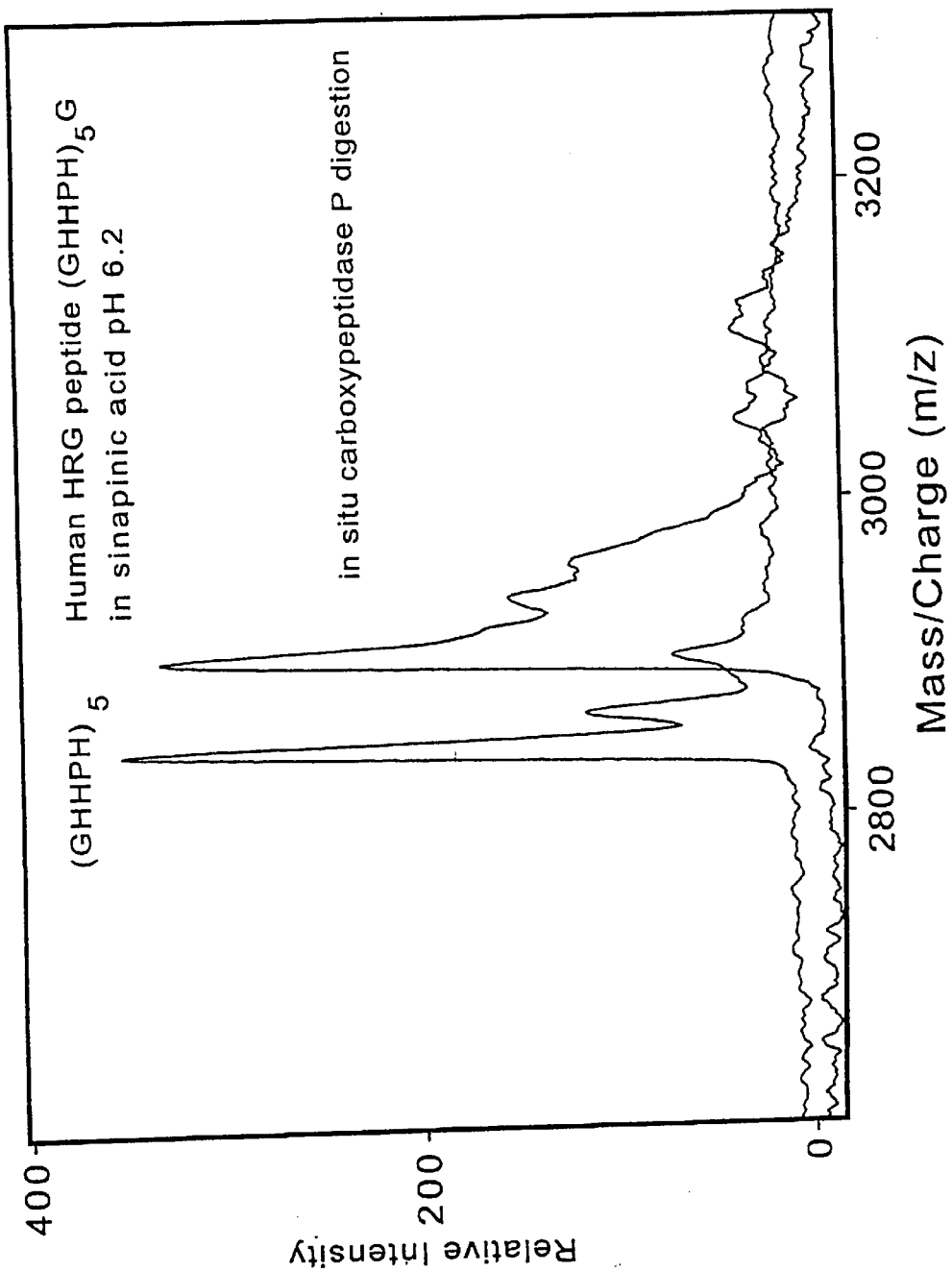
FIG. 3 is a mass spectrum histidine-rich glycoprotein $(GHHPH)_5G$ peptide using sinapinic acid pH 6.2 as the matrix before and after in situ digestion with carboxypeptidase P.

3. Mixture of synthetic peptides as in 1 with sinapinic acid pH 6.2, followed by in situ carboxypeptidase P (1 ul, Boehringer Mannheim Corp, Indianapolis, Ind., 20 ug/50 ul) digestion for 30 min at room temperature. FIG. 3 showed preferential removal of C-terminal amino acid from histidine-rich glycoprotein peptide. Also showed unambiguous C-terminal determination even in peptide mixtures.

Usage of probe Tip (Surface) Materials (Composition) Other Than Stainless Steel or Platinum for Sample Deposition

EXAMPLES

Figure 4:
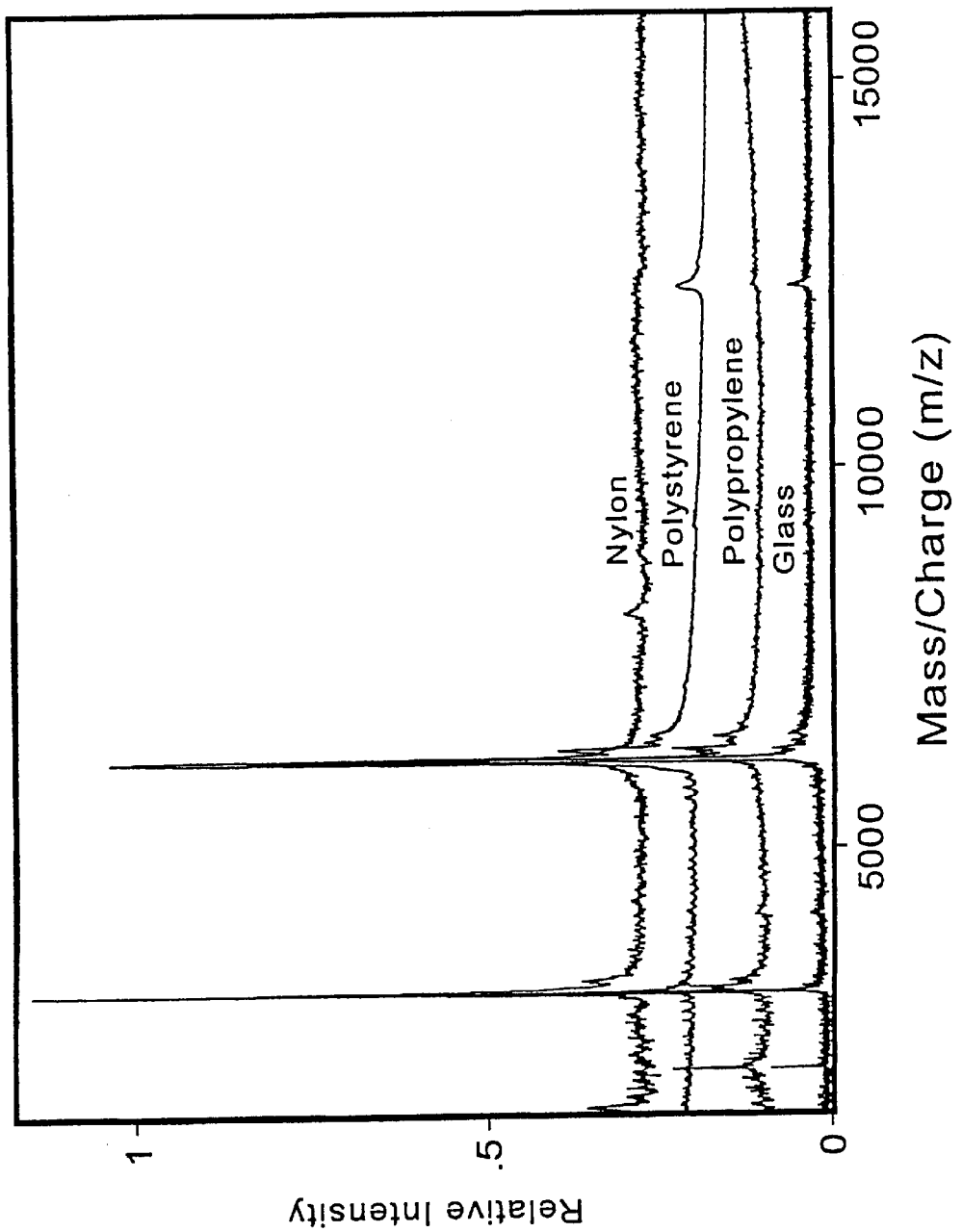
FIG. 4 is a composite mass spectra of peptide mixtures using sinapinic acid as the matrix on glass, polypropylene-coated steel, polystyrene-coated steel and nylon probe tips.

Molten polypropylene or polystyrene was deposited on stainless steel probe tip so as to cover it completely Solid glass rod (1.5 mm dia) was cut into 1 cm segments and inserted into stainless steel probe tip support Solid nylon (Trimmer line, 1.5 mm dia, Arnold, Shelby, Ohio) was cut into 1 cm segments and inserted into stainless steel probe tip support Magnetic stir bars (1.5×8 mm, teflon coated, Curtin Matheson Scientific, Inc., Houston Tex.) inserted into stainless steel probe tip support Peptide mixtures (as in FIG. 1 with dihydroxybenzoic acid in 30% methanol/0.1% TFA) on all four surfaces. FIG. 4

Affinity-directed Laser Desorption (With Matrix Added as Described in Prior Art)

EXAMPLES

Group 1. Immobilized metal ion as the affinity ligand CU(II) was chelated by iminodiacetate group covalently attached to either porous agarose beads (Chelating Sepharose Fast Row, Pharmacia Biotech Inc., Piscataway, N.J., ligand density 22–30 umole/ml gel) or solid TSK-SW beads (ToyoSoda, Japan, ligand density 20 umole/ml gel) Fe(III) was chelated by tris(carboxymethyl) ethylenediamine-Sepharose 6B (synthesized as described by Yip and Hutchens, Protein Expression and Purification 2(1991)355–362, ligand density 65 umole/ml)

Figure 5:
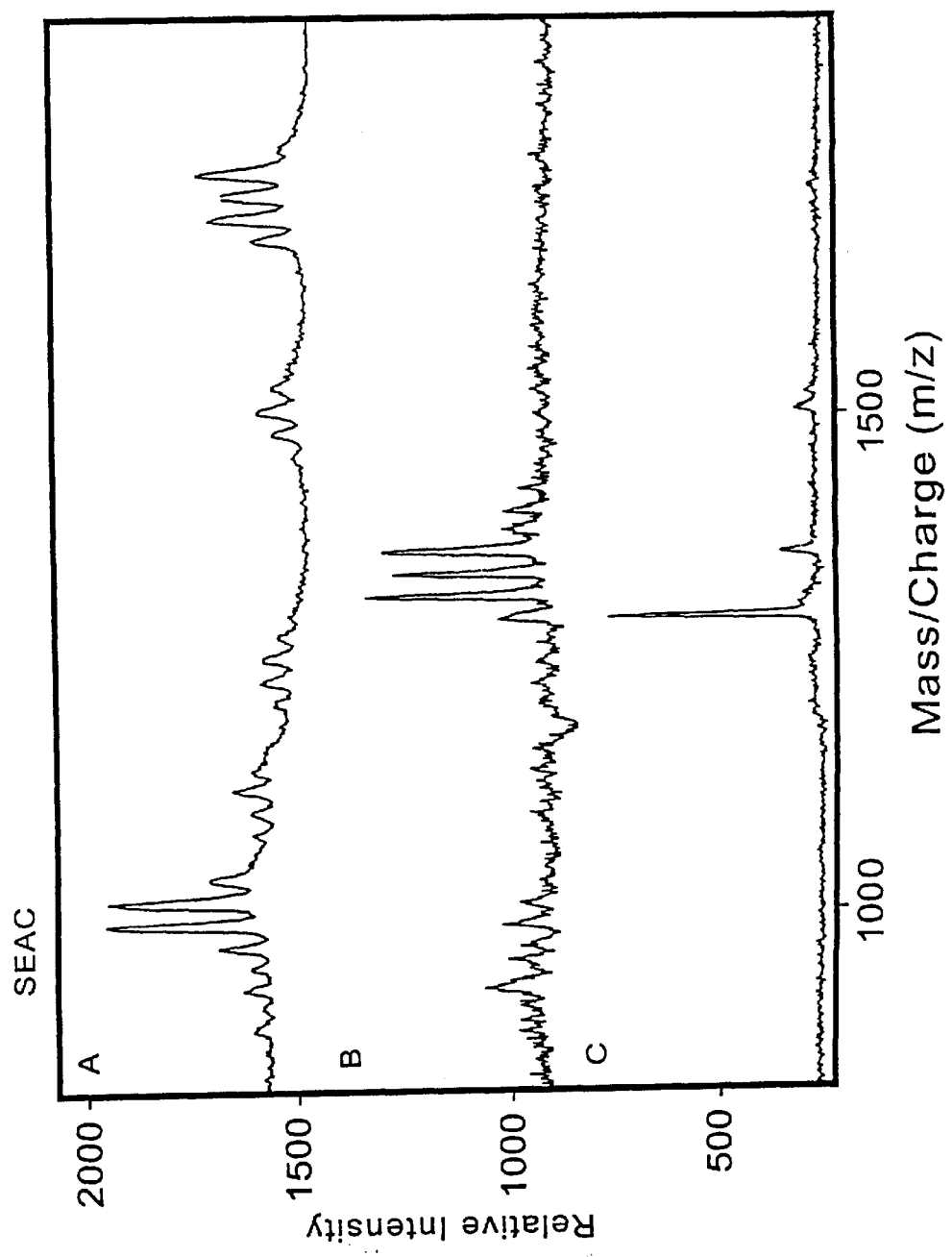
FIG. 5A is a mass spectrum of peptides unadsorbed by TSK SW-IDA-Cu(II).
FIG. 5B is a mass spectrum of peptide adsorbed by TSK SW-IDA-Cu(II).
FIG. 5C is a mass spectrum of the same peptide adsorbed on TSK SW-IDA-Cu(II) after water wash.

1. A mixture of synthetic peptides, neurotensin (30 nmole), sperm activating peptide (50 nmole) and angiotensin I (150 nmole), were mixed with 50 ul packed volume of TSK SW-DA-Cu(II) at pH 7.0 (20 mM sodium phosphate, 0.5 M NaCl) at room temperature for 10 min. The gel was then washed with 3×200 ul sodium phosphate buffer, containing 0.5 M NaCl, pH 7.0 and suspended in equal volume of water. 2 ul of the gel suspension was mixed with 1 ul sinapinic acid (methanol). FIG. 5A showed the molecular ions (and multiple Na-adducts) of neurotensin and sperm activating factor which were not adsorbed by the IDA-Cu (II). The mass spectrum in FIG. 5B showed mainly the, angiotensin I plus Na-adducts. When the IDA-Cu(II) gel was further washed with 500 ul of water 2×, the resulting mass spectrum showed only the parent angiotensin I species with no other adduct peaks. When the IDA-Cu(II) gel beads with adsorbed angiotensin was incubated with cyanohydroxycinnamic acid (20 mg/ml water) pH 7.0 for 10 min at room temperature and then analyzed separately, the angiotensin I was found to be still associated with the gel beads and not with the matrix solution.

Figure 6:
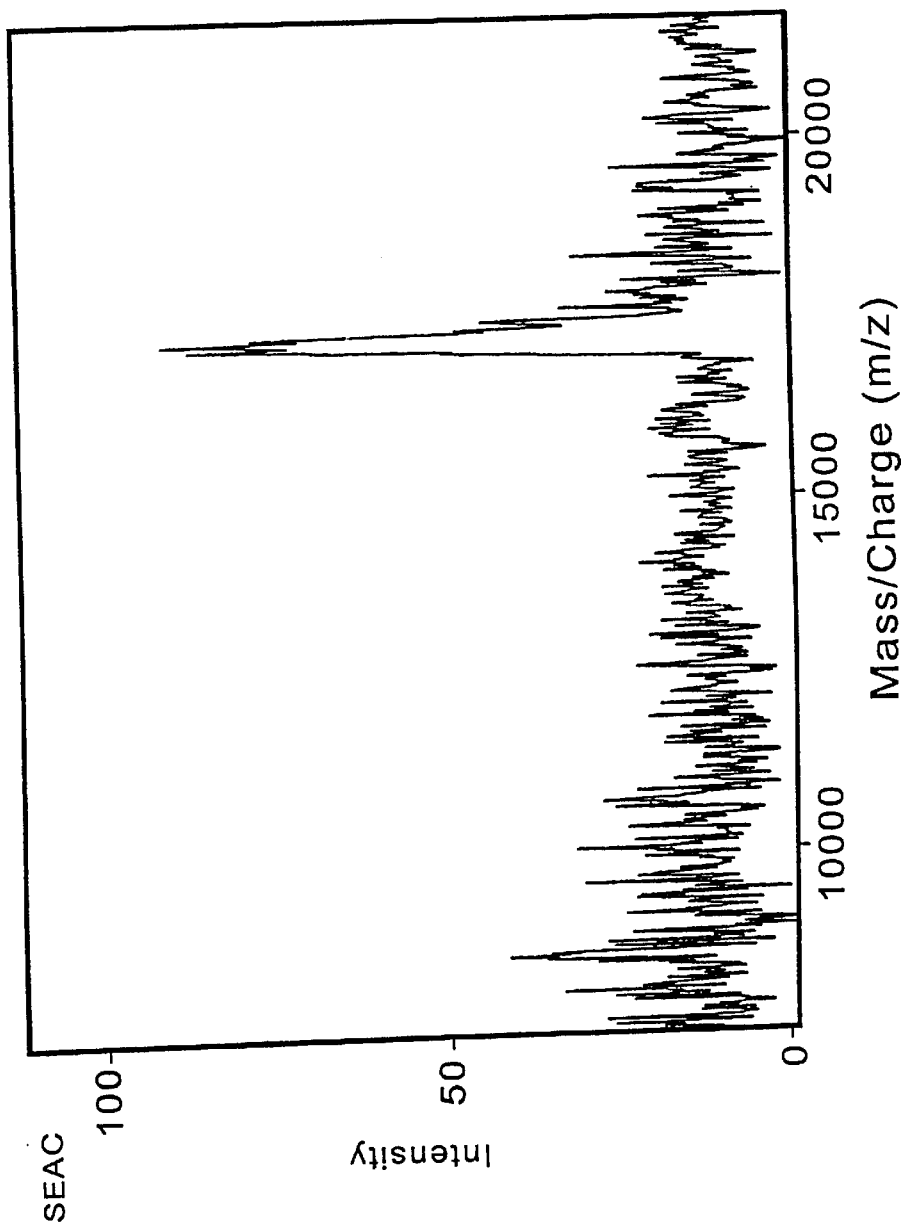
FIG. 6 is a mass spectrum of myoglobin ($\leq 8$ fmole) affinity-adsorbed on TSK SW-IDA-Cu(II).

2. Horse heart myoglobin (325 pmole) was mixed with 50 ul of TSK SW-IDA-Cu(II) gel beads in 20 mM sodium phosphate, 0.5 M NaCl, pH 7.0 at room temperature for 10 min. The gel beads were then washed with 2×500 ul of buffer and 2×500 ul of water. The beads were suspended in equal volume of water and then serial diluted into water. 0.5 ul of the diluted gel suspension was mixed with 1 ul of sinapinic acid (30% methanol/0.1% TFA). A detectable signal (after averaging 50 laser shots) of myoglobin was still obtained when the calculated quantity equivalent to or less than 8 fmole was deposited on the probe tip. FIG. 6

Figure 7:
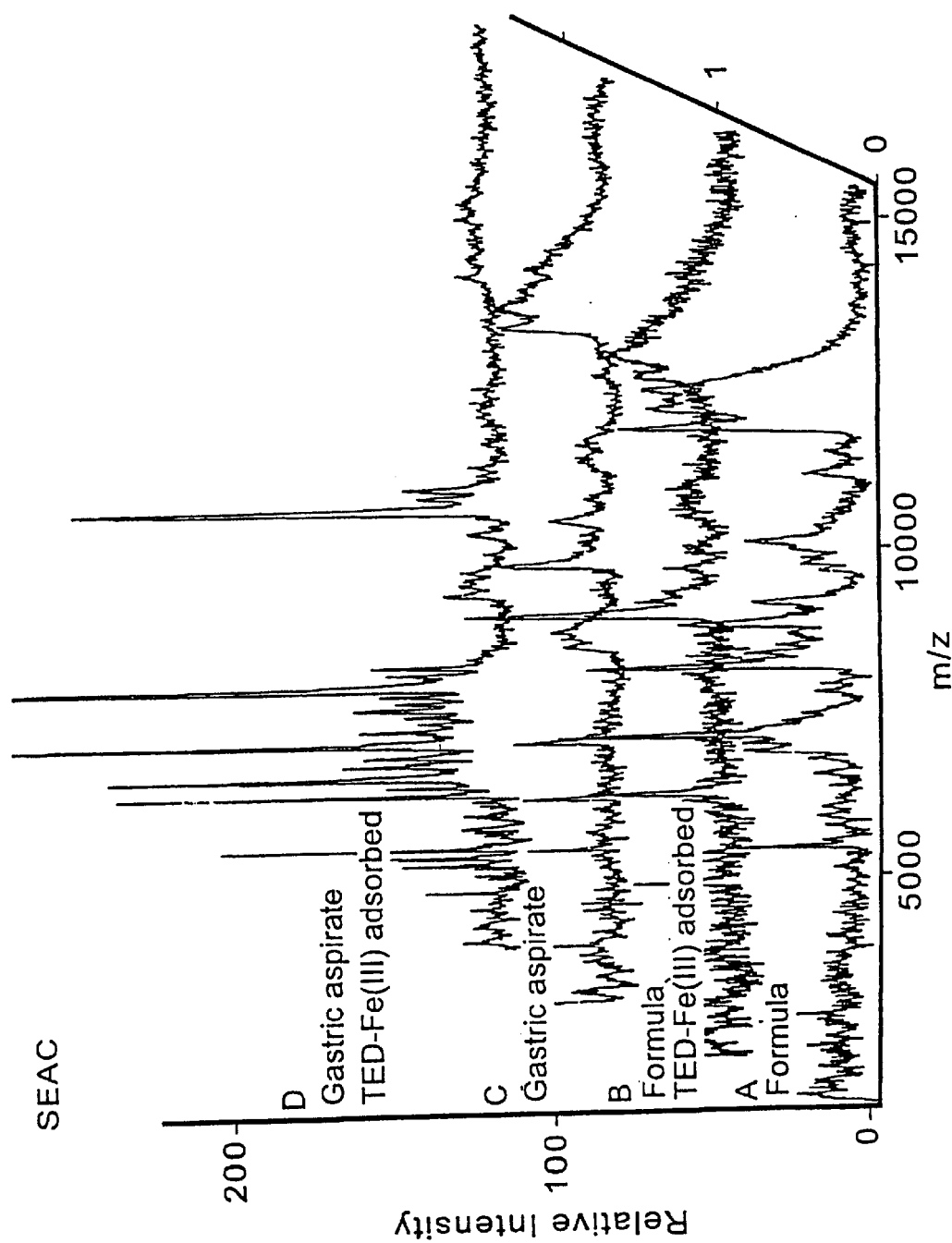
FIG. 7A is a mass spectrum of proteins/peptides in infant formula.
FIG. 7B is a mass spectrum of phosphopeptides in the same sample affinity-adsorbed on Sepharose-TED-Fe(III).
FIG. 7C is a mass spectrum of proteins/peptides in gastric aspirate of preterm infant.
FIG. 7D is a mass spectrum of the phosphopeptides in the same sample adsorbed on Sepharose-TED-Fe(III).

3. 100 ul of infant formula and gastric content of preterm infant aspirated 90 min after feeding of infant formula was mixed with 50 ul of TED-Fe(III) in 0.1 M MES, 0.15 M NaCl, pH 6.5 at room temperature for 15 min. The gel beads were then washed with 3×500 ul of MES buffer and then with 1×500 ul of water. 1 ul of the gel suspension was mixed with 2 ul of sinapinic acid (50% acetonitrile/0.1% TFA). The result showed that gastric aspirate had much more low molecular weight phosphopeptides (i.e., bound by TED D,—Fe(III)) than the formula due to proteolytic digestion. In situ alkaline phosphatase digestion of peptides adsorbed on the TED-Fe(III) gel beads showed shifts to lower molecular weight indicating that they are indeed phosphopeptides. FIG. 7

Group 2. Immobilized antibody as the affinity ligand
Polyclonal rabbit anti-human lactoferrin antibody was custom generated for this lab by Bethyl Laboratories (Montgomery, Tex). It was purified by thiophilic adsorption and then by immobilized lactoferrin column. Sheep anti-rabbit IgG covalently attached to magnetic beads were obtained from Dynal AS (Oslo, Norway) (uniform 2.8 um superparamagnetic polystyrene beads, ligand density 10 ug sheep IgG per mg bead).

Figure 8:
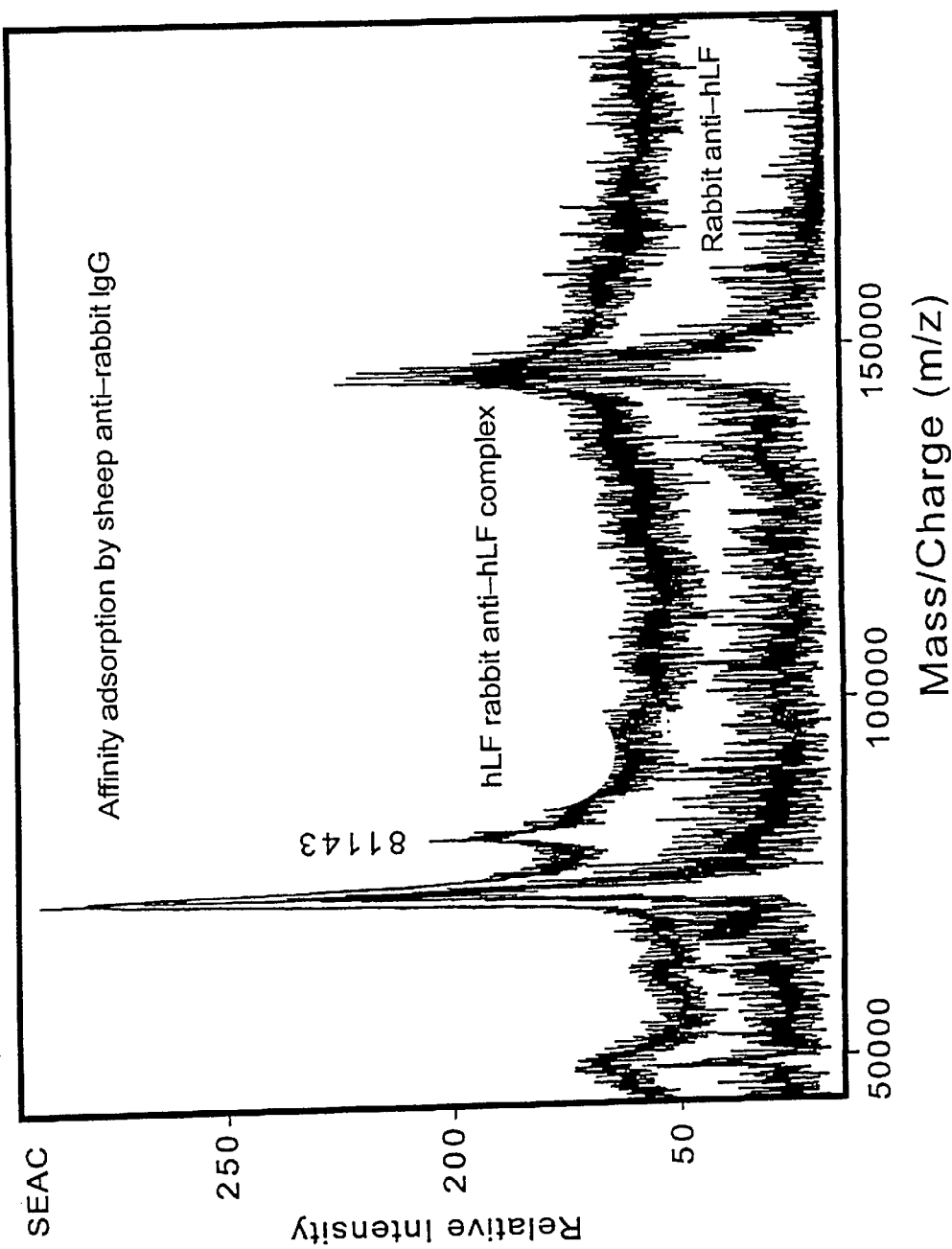
FIG. 8 (bottom) is a mass spectrum of rabbit anti-human lactoferrin immunoglobin affinity adsorbed on paramagnetic Dynabead-sheep anti-rabbit IgG.

1. Human lactoferrin (1 nmole) was incubated with rabbit antihuman lactoferrin at 37° for 30 min. Subsequently, 40 ul of sheep anti-rabbit IgG on Dynabeads ($6-7 \times 10^8$ beads/ml) was added and incubated at 37° for 30 min. The beads were then washed with 3×500 ul of sodium phosphate buffer, and 2×500 ul of water. The final amount of human lactoferrin bound to the complex was estimated to be 4 pmole. Approximately 1/10 of the beads was transferred to a magnetic probe tip and mixed with 2 ul of sinapinic acid (30% MeOH/0.1% TFA). Result showed the lactoferrin ion signal in addition to the rabbit IgG signal. FIG. 8

Group 3. Immobilized nucleic acid as the affinity ligand
Single-strand DNA immobilized on 4% agarose beads was obtained from GIBCO BRL, Gaithersburg, Md. The ligand density was 0.5–1.0 mg/ml.

Figure 9:
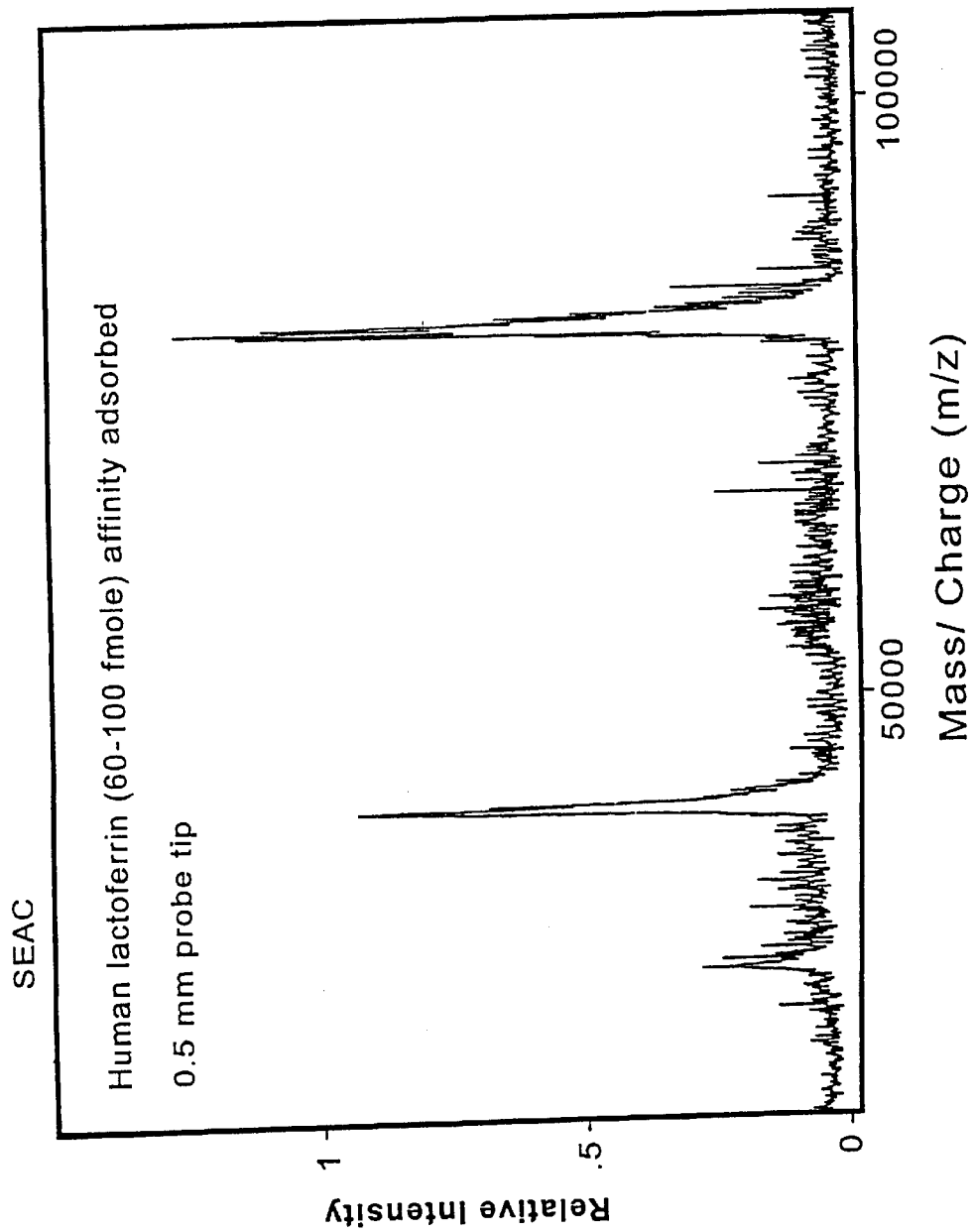
FIG. 9 is a mass spectrum of human lactoferrin affinity adsorbed on a single bead of agarose-single-stranded DNA deposited on a 0.5 mm diameter steel probe tip.

1. 200 ul of $^{125}$I human lactoferrin (equivalent to 49 nmole) was mixed with 100 ul of immobilized single-strand DNA in 20 mM HEPES, pH 7.0 at room temperature for 10 min. The beads were then washed with 5×500 ul of HEPES buffer and then suspended in equal volume of water. The amount of lactoferrin bound per bead was found to be 62 fmole by determining the radioactivity and counting the number of beads per unit volume. Various numbers of beads (from 1 to 12) were deposited on 0.5 mm diameter probe tips and mixed with 0.2 ul of sinapinic acid (30% methanol/0.1% TFA). Lactoferrin ion signals were obtained with multiple 100 laser shots on a single bead with adsorbed lactoferrin. FIG. 9

Figure 10:
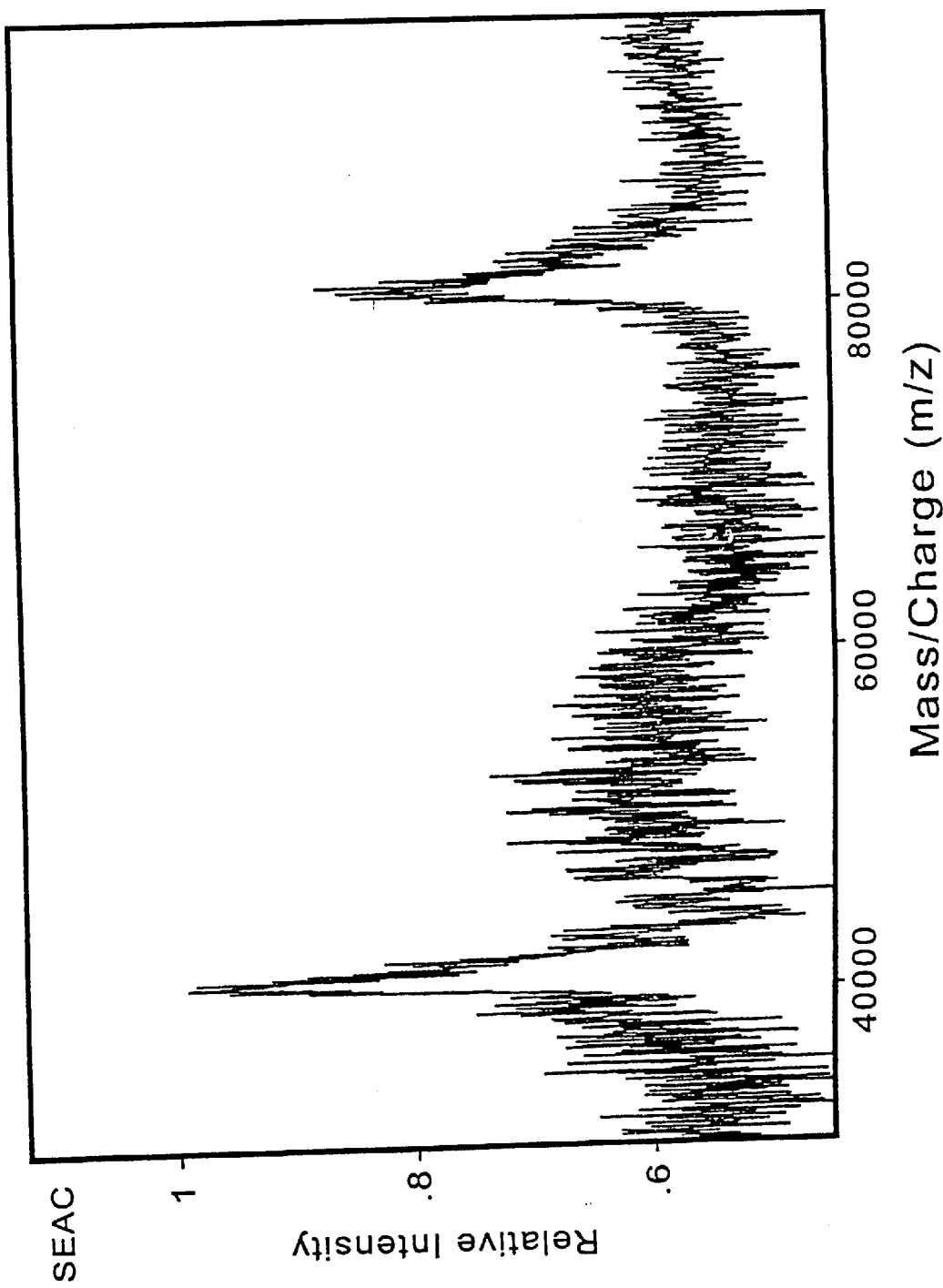
FIG. 10 is the mass spectrum of human lactoferrin affinity adsorbed from urine on agarose-single-stranded DNA.

2. 30 pmole of $^{59}$Fe-human lactoferrin was added to 1 ml of preterm infant urine and mixed with 20 ul of immobilized single-strand DNA on agarose in 0.1 M HEPES pH 7.4 at room temperature for 15 min. The beads were washed with 2×500 ul HEPES buffer, and 2×500 ul of water. The beads were then suspended in equal volume of water and 1 ul (equivalent to not more than 350 fmole as determined by radioactivity) was mixed with 1 ul sinapinic acid (30% methanol/0.1% TFA) on a probe tip. Positive lactoferrin signals were obtained for multiple 50 laser shots. FIG. 10

Group 4. Immobilized biomolecule as the affinity ligand
Soybean trypsin inhibitor (Sigma, St Louis, Mo.) was immobilized on AffiGel 10 (BioRad Laboratories, Hercules, Calif., ligand density 15 umole/ml) according to manufacturer's instructions.

Figure 11A:
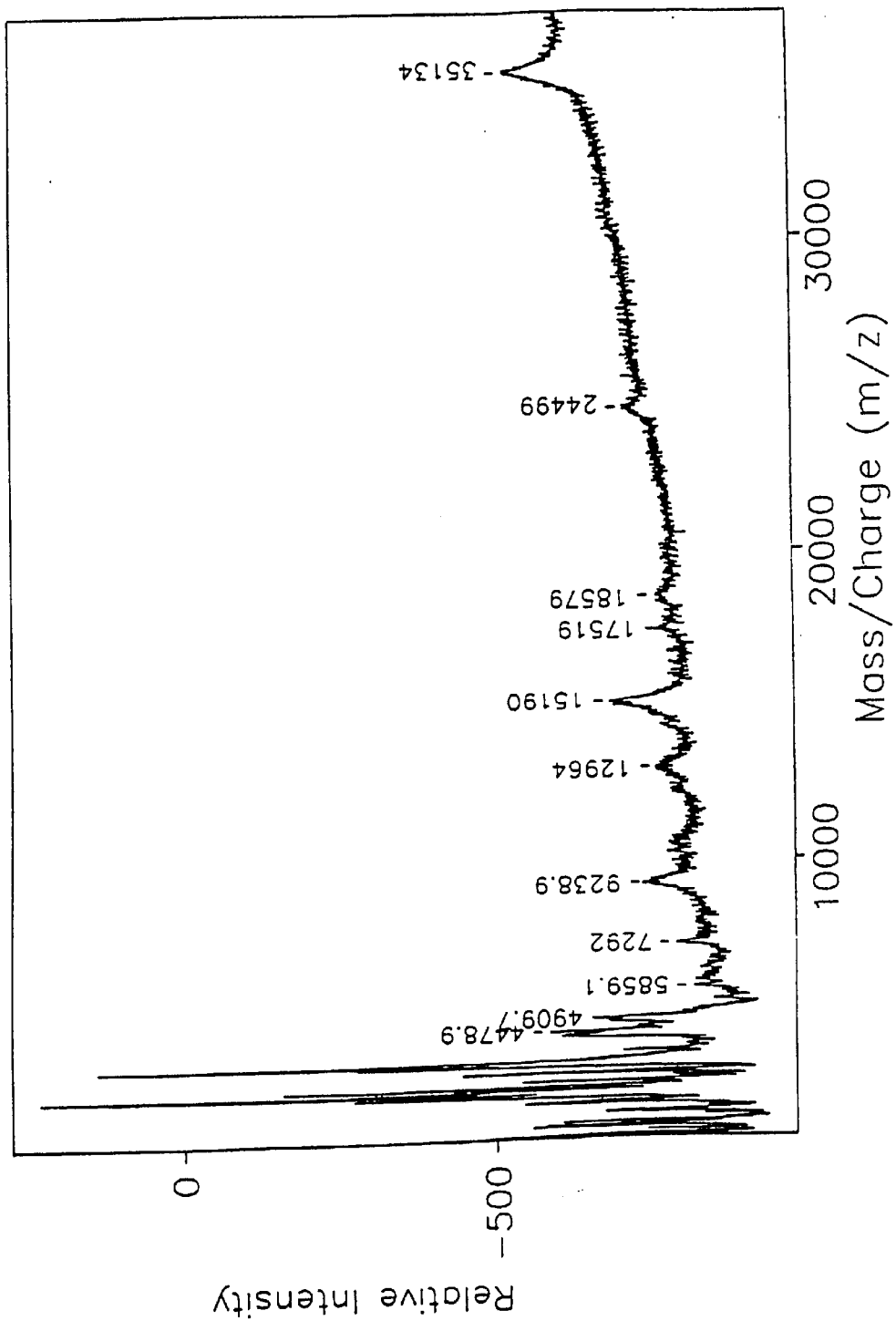
FIG. 11A is a mass spectrum of human gastrointestinal fluid.
Figure 11B:
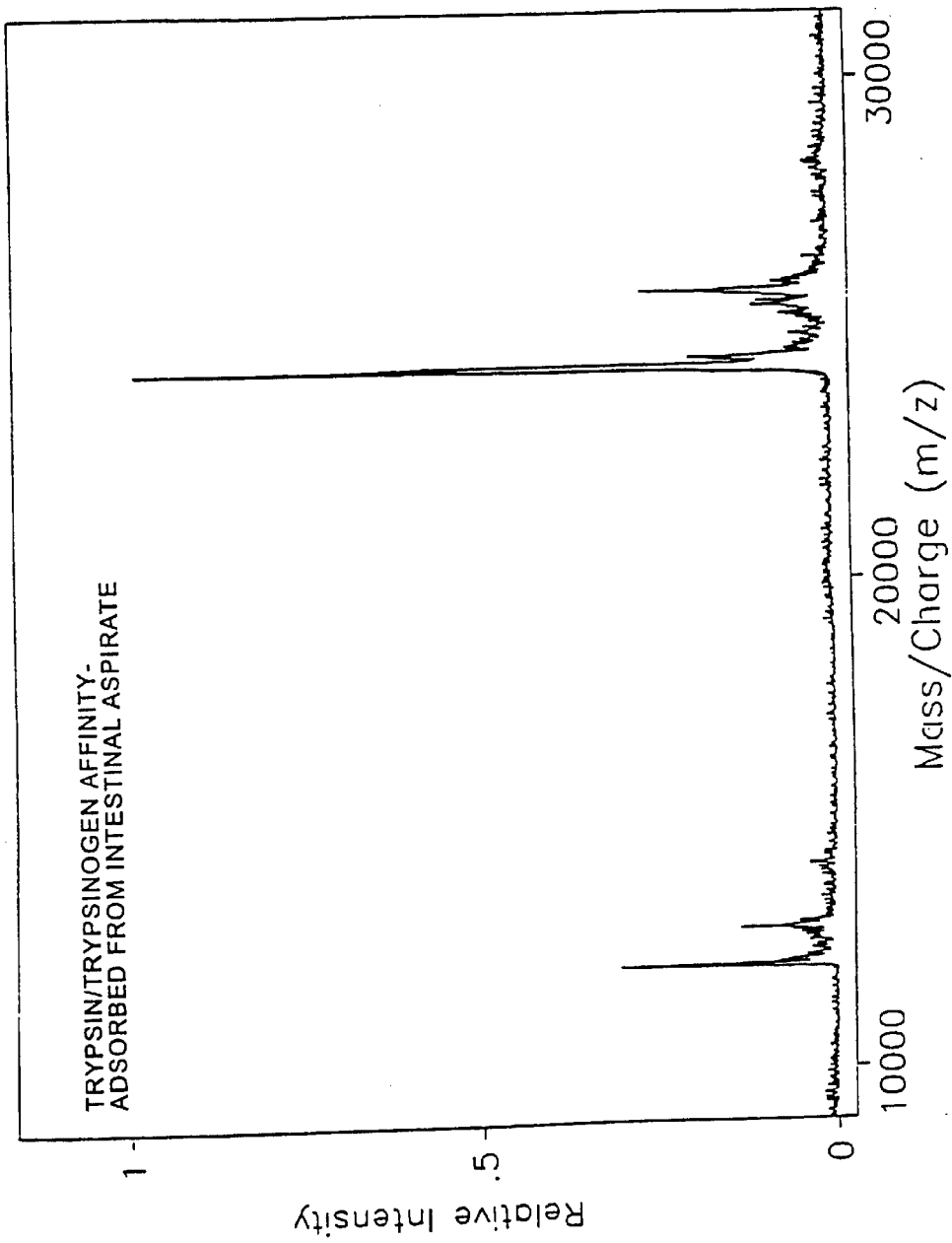
FIG. 11B is a mass spectrum of trypsin in the same sample affinity adsorbed on AffiGel 10-soybean trypsin inhibitor.

1. 100 ul of human gastrointestinal aspirate was mixed with 50 ul of immobilized soybean trypsin inhibitor in 20 mM sodium phosphate, 0.5 M sodium chloride, pH 7, at room temperature for, 15 min. The gel beads were then washed with 3×500 ul of phosphate buffer, and 2×500 ul of water. 1 ul of gel bead suspension was mixed with 2 ul of sinapinic acid (50% acetonitrile/0.1% TFA). Result showed the presence of trypsin and trypsinogen in the aspirate. FIG. 11

Group 5. Immobilized dye as the affinity ligand
Cibacron Blue 3GA-agarose (Type 3000, 4% beaded agarose, ligand density 2–5 umoles/ml, Sigma).

Other immobilized dyes include Reactive Red 120-agarose, Reactive Blue-agarose, Reactive Green-agarose, Reactive Yellow-agarose (Sigma)

Figure 12:
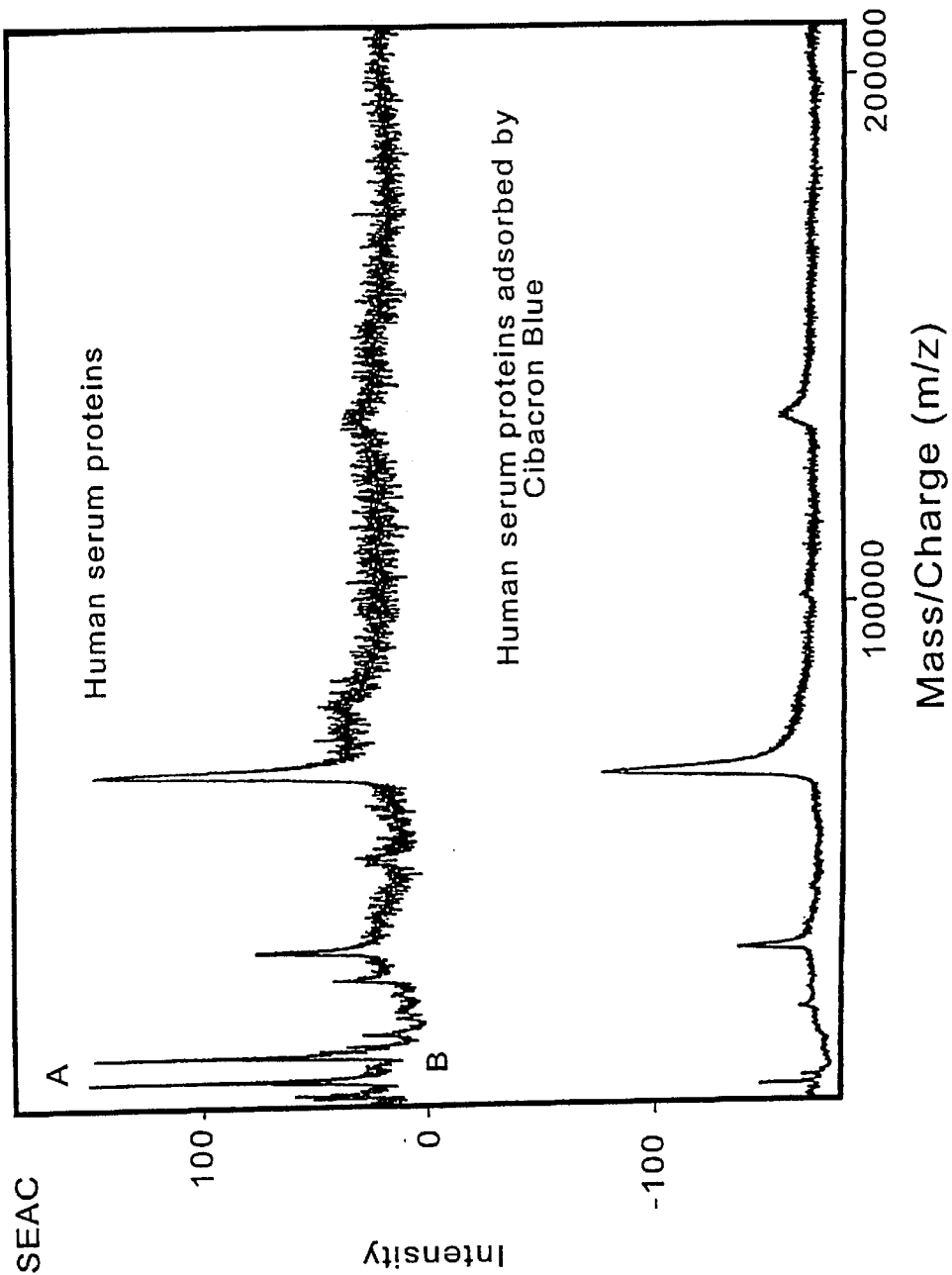
FIG. 12A is a mass spectrum of human serum proteins.
FIG. 12B is a mass spectrum of human serum albumin in the same sample affinity adsorbed on agarose-Cibacron blue.

1. 200 ul of human plasma was mixed with 50 ul of immobilized dye in 20 mM sodium phosphate, 0.5 M NaCl, pH 7.0 at room temperature for 10 min. The gel beads were then washed with 3×500 ul of phosphate buffer and 2×500 ul of water. 1 ul of gel bead suspension was mixed with 2 ul of sinapinic acid (50% acetonitrile/0.1% TFA). Result showed the selective adsorption of human serum albumin from the serum sample by Cibacron Blue. FIG. 12
Surface-enhanced Laser Desorption

EXAMPLES

Group 1. Energy-absorbing molecule covalently bonded to surface via the N-group

Figure 13:
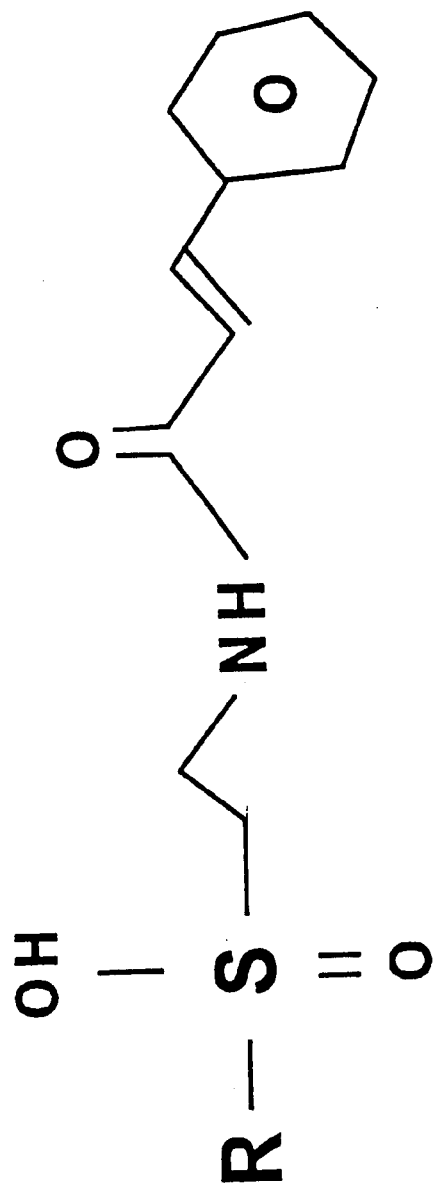
FIG. 13 is a drawing of the surface bound cinnamamide; R represents the surface plus cross-linear.
Figure 14:
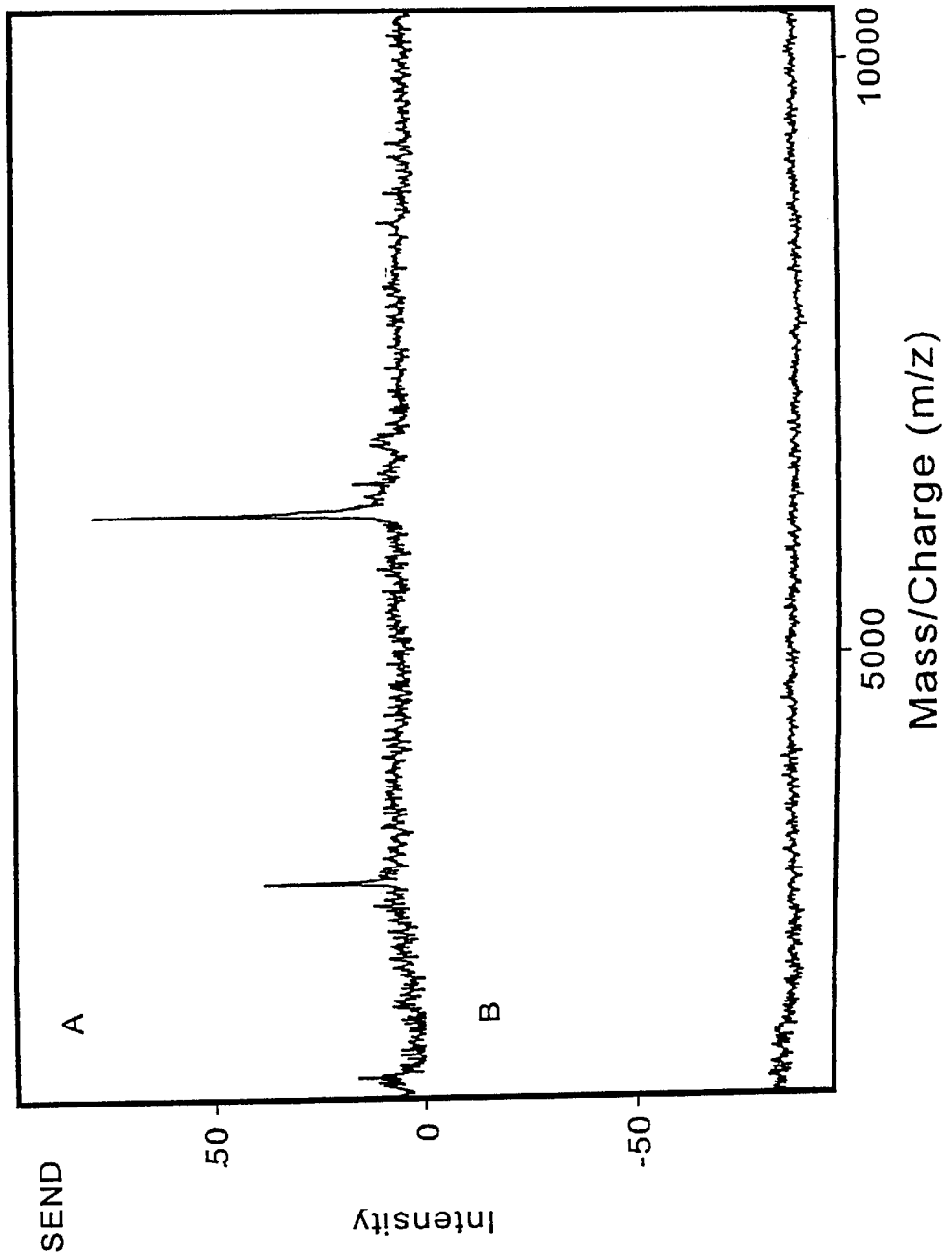
FIG. 14A is a mass spectrum of peptide mixtures on surface bound cinnamamide.
FIG. 14B shows the mass spectrum of the same peptide mixtures on free cinnamamide.

Cinnamamide (Aldrich, not a matrix by prior art) was dissolved in isopropanol/0.5 M sodium carbonate (3:1) and mixed with divinyl sulfone (Fluka, Ronkonkoma, N.Y.) activated Sepharose (Pharmacia) at room temperature for 2 hr. The excess molecules were washed away with isopropanol. The proposed structure was presented in FIG. 13. 2 ul of bound or free molecule was deposited on the probe tips, 1 ul of peptide mixtures in 0.1% TFA was added on top and the result showed the peptide ion signals detected only for the bound form. FIG. 14.

Group 2. Energy absorbing molecule covalently bonded to surface via the C-group

Figure 15:
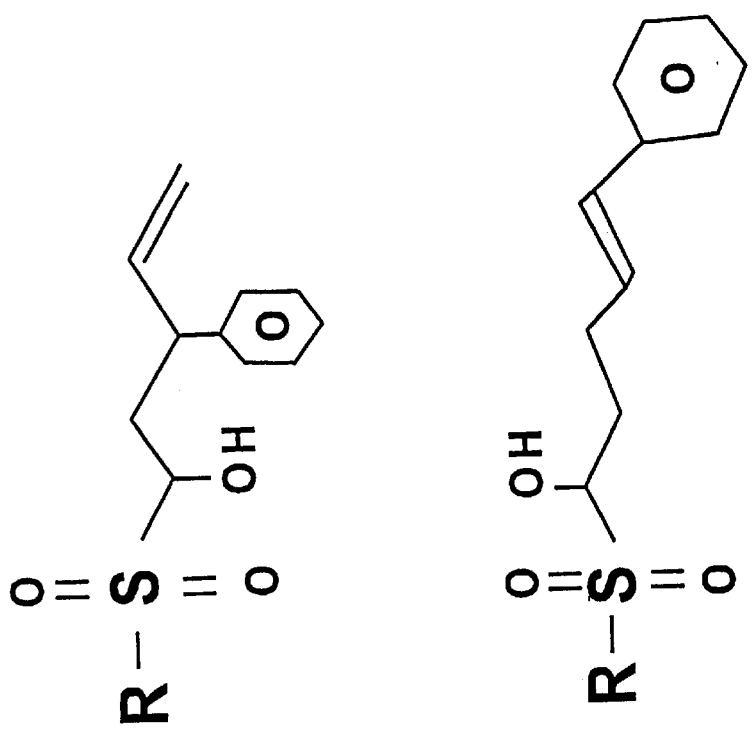
FIG. 15 is a drawing of the surface bound cinnamyl bromide; two structural forms are possible; R represents the surface plus cross-linear.
Figure 16:
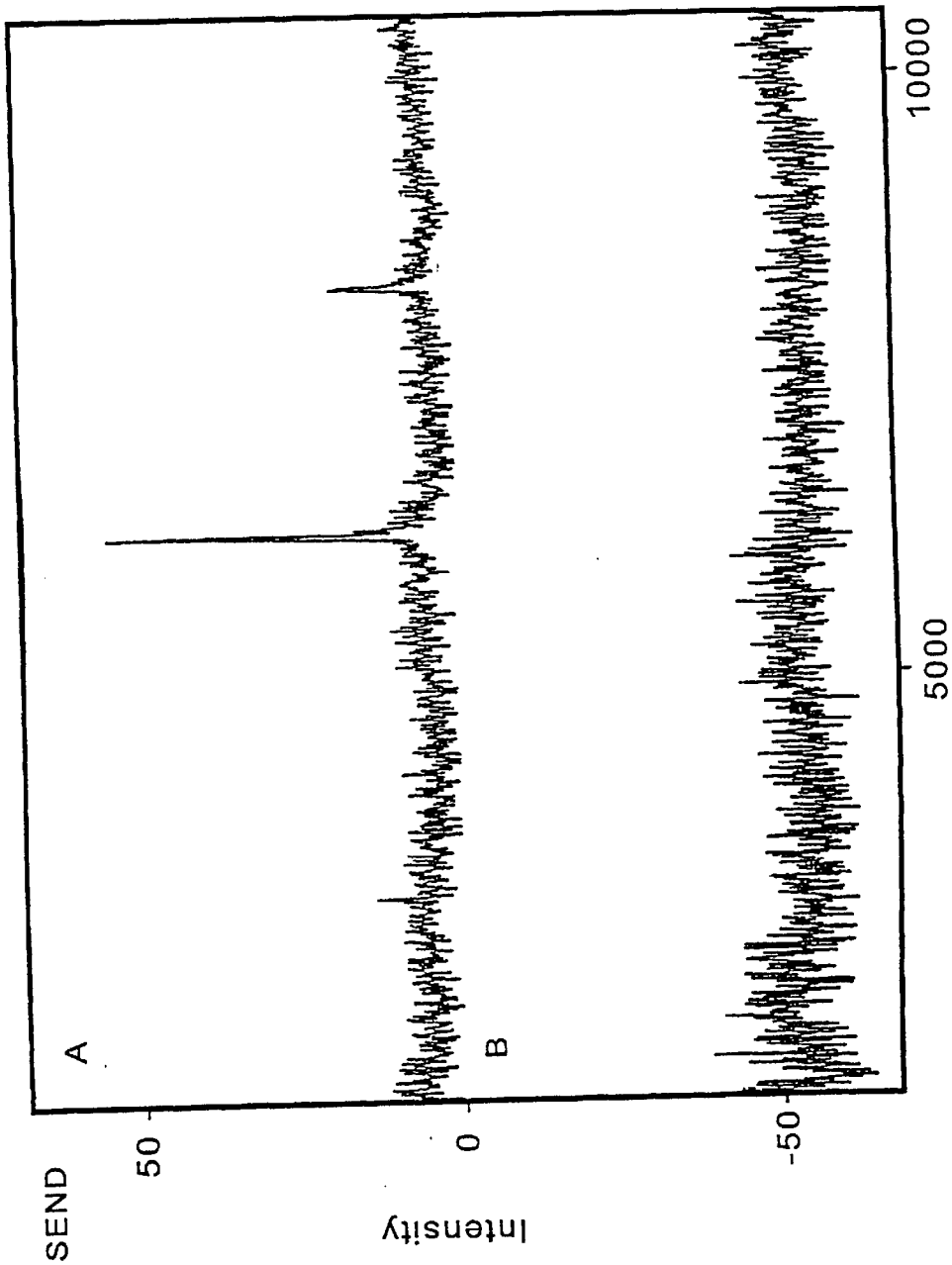
FIG. 16A is a mass spectrum of peptide mixtures on surface bound cinnamyl bromide.
FIG. 16B is a mass spectrum of the same peptide mixtures on free cinnamyl bromide.

Cynnamyl bromide (Aldrich, not a matrix by prior art) was dissolved in isopropanol/0.5 M sodium carbonate and mixed with divinyl sulfone-activated Sepharose at room temperature overnight. The excess molecules were washed away with isopropanol. The proposed structures are presented in FIG. 15. 2 ul of the bound or free molecule was deposited on the probe tip, 1 ul of peptide mixtures in 0.1% TFA was added on top and the result showed the detection of peptide ion signal only for the bound form. FIG. 16.

Group 3. Energy-absorbing molecule covalently bonded to surface via the C-group

Figure 17:
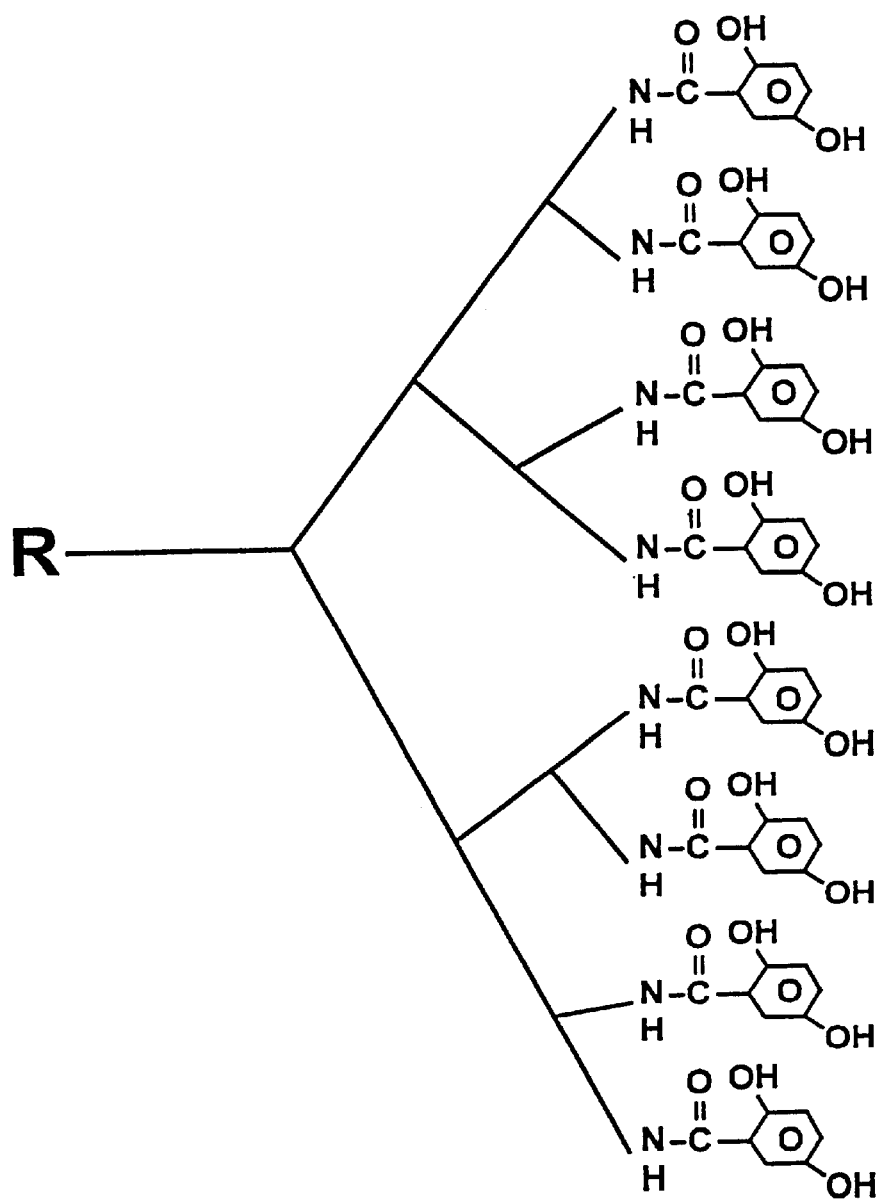
FIG. 17 is a drawing of the surface bound MAP-dihydroxybenzoic acid; R represents the surface plus cross-linear.
Figure 18:
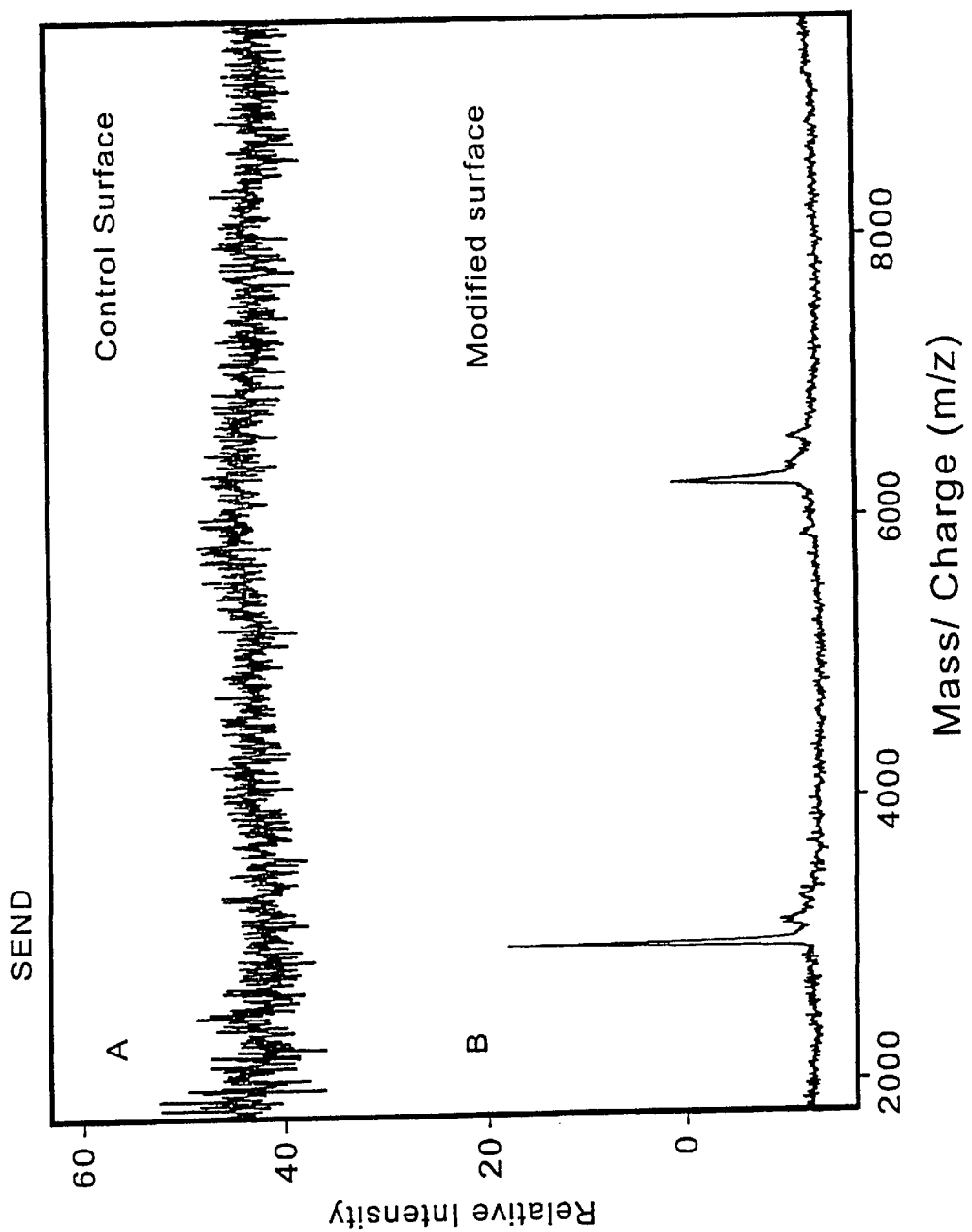
FIG. 18 is a mass spectrum of peptide mixtures on surface bound MAP alone (control surface).

Dihydroxybenzoic acid was activated by carbodiimide and mixed with Fmoc-MAP 8 branch resin (Applied Biosystems, Forster City, Calif.) overnight. The proposed structure was presented in FIG. 17. After washing, 1 ul of the bonded molecule on MAP or the MAP alone in 50% acetonitrile/0.1% TFA were deposited on the probe tip, 1 ul of peptide mixture was added on top, the resulting mass spectrum was presented in FIG. 21.

Group 4. Energy absorbing molecule covalently bonded to surface via undetermined group.

Figure 19A:
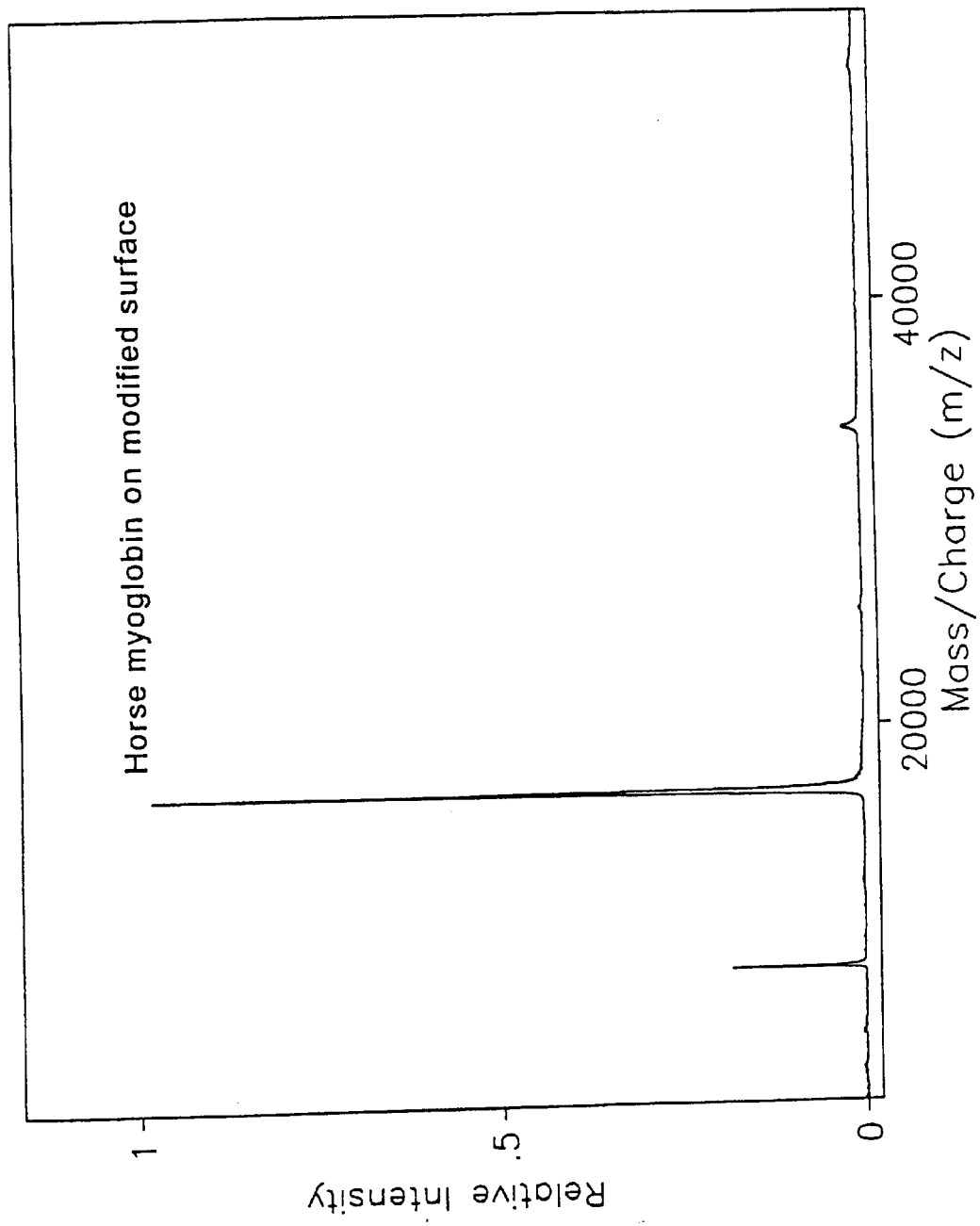
FIG. 19A is a mass spectrum of myoglobin on surface bound cyanohydroxycinnamic acid.
Figure 19B:
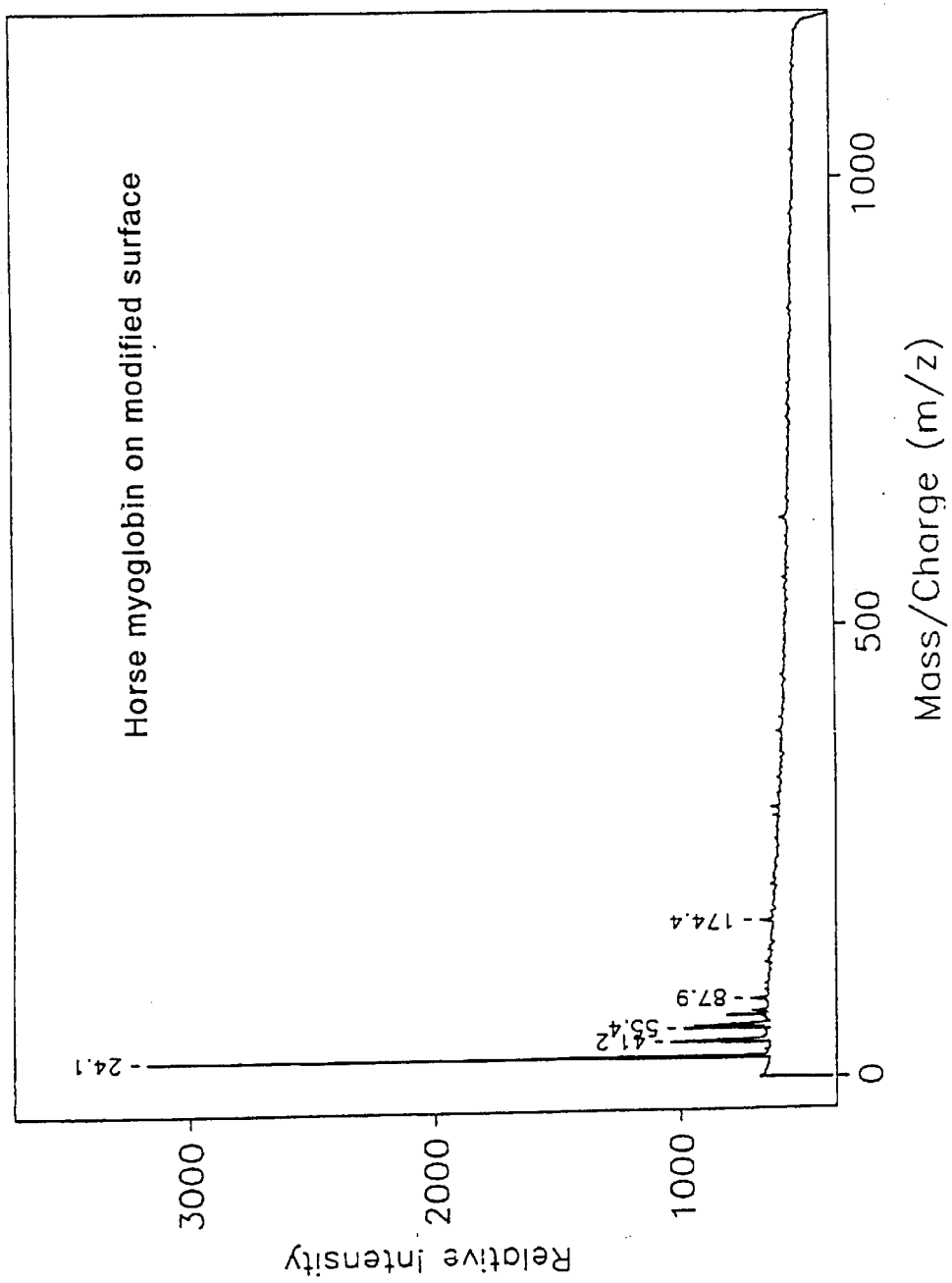
FIG. 19B is the same mass spectrum in the low mass region.

Cyanohydroxycinnamic acid was dissolved in methanol and mixed with AffiGel 10 (BioRad) at room temperature for two hours. The unbound molecules were washed away with methanol. Protein samples that are found to desorb successfully from this modified surface include myoglobin (FIG. 19), trypsin and carbonic anhydrase.

These examples (Groups 1–4) are also demonstrations of combined surface-enhanced and affinity-directed desorption where the adsorbed (bonded) energy absorbing molecular also act as affinity adsorption reagents to enhance the capture of analyte molecules.

Definitions:

(1) "Presenting surface"—the probe tip, sample plate or other surface on which the analyte and matrix are presented for desorption/ionization and analysis for example by mass spectrometry.

(2) "Matrix"—as described in prior art as the substance mixed with the analyte (typically prior to deposition) and deposited on the presenting surface in association with the analyte to absorb at least part of the energy from the energy source (e.g., laser) to facilitate desorption of intact molecules of the analyte.

(3) "Analyte"—the material which is the subject of desorption and investigation by mass spectrometry or other means for detection.

(4) "Affinity reagent" (analyte capture device)—the class of molecules (both man made, unnatural, natural and biological) and/or compounds which have the ability of being retained on the presenting surface (by covalent bonding, chemical absorption, etc.) while retaining the ability of recognition and bonding to an analyte.

(5) "Desorption"—the departure of analyte from the surface and/or the entry of the analyte into a gaseous phase.

(6) "Ionization"—the process of creating or retaining on an analyte an electrical charge equal to plus or mints one or more electron units.

(7) "Adduct"—the appearance of an additional mass associated with the analyte and usually caused by the reaction of excess matrix (or matrix break-down products) directly with the analyte.

(8) "Adsorption"—the chemical bonding (covalent and/or noncovalent) of the energy-absorbing molecules, the affinity reagent (i.e., analyte capture device), and/or the analyte to the probe (presenting surface).

What is claimed:

1. A method for detecting an analyte comprising the steps of:
   (a) capturing the analyte from a sample on a sample presenting surface of a mass spectrometer probe, wherein the surface is derivatized with an affinity reagent that binds the analyte, wherein the affinity reagent is immobilized by covalent bonding to the sample presenting surface;
   (b) applying matrix to the analyte on the sample presenting surface; and
   (a) detecting the captured analyte by laser desorption/ionization mass spectrometry without substantial destruction of the analyte by the laser.

2. The method of claim 1 wherein the sample is a biological sample.

3. The method of claim 1 wherein the analyte comprises a protein or peptide.

4. The method of claim 1 wherein the analyte comprises a nucleic acid.

5. The method of claim 1 wherein the analyte comprises a carbohydrate.

6. The method of claim 1 wherein the matrix is selected from the group consisting of cyanohydxoxycinammic acid, nicotinic acid, sinapinnic acid and dihydroxybenzoic acid.

7. The method of claim 1 further comprising washing the sample presenting surface after step (a).

8. A mass spectrometer probe comprising:
   (a) a sample presenting surface derivatized with an affinity reagent that is capable of binding an analyte, wherein the affinity reagent is immobilized by covalent bonding to the sample presenting surface;
   (b) an analyte captured by the affinity reagent; and
   (c) a matrix applied to the analyte, whereby the analyte is not substantially destroyed by a laser beam.

9. The probe of claim 8 wherein the analyte comprises a protein or peptide.

10. The probe of claim 8 wherein the analyte comprises a nucleic acid.

SEQUENCE LISTING

```
<160> NUMBER OF SEQ ID NOS: 2

<210> SEQ ID NO 1
<211> LENGTH: 11
<212> TYPE: PRT
<213> ORGANISM: Homo sapiens

<400> SEQUENCE: 1

Gly His His Pro His Gly His His Pro His Gly
1               5                   10

<210> SEQ ID NO 2
<211> LENGTH: 26
<212> TYPE: PRT
<213> ORGANISM: Homo sapiens

<400> SEQUENCE: 2

Gly His His Pro His Gly His His Pro His Gly His His Pro His Gly
1               5                   10                  15

His His Pro His Gly His His Pro His Gly
            20                  25
```

11. The probe of claim 8 wherein the analyte comprises a carbohydrate.

12. The probe of claim 8 wherein comprising a plurality of affinity reagents arranged in predetermined arrays.

13. The probe of claim 8 wherein the matrix is selected from the group consisting of cyanohydroxycinammic acid, nicotinic acid, sinapinnic acid and dihydroxybenzoic acid.

14. A mass spectrometer apparatus comprising:
  (a) a mass spectrometer probe comprising:
    (i) a sample presenting surface derivatized with an affinity reagent that is capable of binding an analyte, wherein the affinity reagent is immobilized by covalent bonding to the sample presenting surface;
    (ii) an analyte captured by the affinity reagent; and
    (iii) a matrix applied to the analyte;
  (b) a laser source that directs laser energy to the sample presenting surface for desorbing and ionizing the analyte, wherein the analyte is not substantially destroyed by the laser;
  (c) means for applying an accelerating electrical potential to the desorbed, ionized analyte; and
  (d) a detector that detects the desorbed, ionized analyte.

15. The mass spectrometer apparatus of claim 14 wherein the analyte comprises a protein or peptide.

16. The mass spectrometer apparatus of claim 14 wherein the analyte comprises a nucleic acid.

17. The mass spectrometer apparatus of claim 14 wherein the analyte comprises a carbohydrate.

18. The mass spectrometer apparatus of claim 14 wherein the probe comprises a plurality of affinity reagents arranged in predetermined arrays.

19. The mass spectrometer apparatus of claim 14 wherein the laser is selected from a nitrogen laser and an Nd-YAG laser.

20. The mass spectrometer apparatus of claim 14 wherein the matrix is selected from the group consisting of cyanohydroxycinammic acid, nicotinic acid, sinapinnic acid and dihydroxybenzoic acid.

* * * * *

(12) EX PARTE REEXAMINATION CERTIFICATE (5972nd)
United States Patent
Hutchens et al.

(10) Number: US 6,734,022 C1
(45) Certificate Issued: *Oct. 23, 2007

(54) METHOD AND APPARATUS FOR DESORPTION AND IONIZATION OF ANALYTES

(75) Inventors: T. William Hutchens, Los Altos, CA (US); Tai-Tung Yip, Cupertino, CA (US)

(73) Assignee: Baylor College of Medicine, Houston, TX (US)

Reexamination Request:
No. 90/007,449, Mar. 4, 2005

Reexamination Certificate for:
Patent No.: 6,734,022
Issued: May 11, 2004
Appl. No.: 09/809,657
Filed: Mar. 15, 2001

(*) Notice: This patent is subject to a terminal disclaimer.

Related U.S. Application Data

(63) Continuation of application No. 08/068,896, filed on May 28, 1993, now abandoned.

(51) Int. Cl.
*H01J 49/10* (2006.01)
*H01J 49/16* (2006.01)
*H01J 49/04* (2006.01)
*H01J 49/02* (2006.01)
*G01N 24/00* (2006.01)

(52) U.S. Cl. .................. 436/173; 436/155; 436/174; 436/178; 435/7.1; 536/25.4; 250/287

(58) Field of Classification Search ............. 436/173, 436/174, 178, 155; 250/287; 435/7.1; 536/25.4; 530/300
See application file for complete search history.

(56) References Cited

U.S. PATENT DOCUMENTS 5,002,883 A * 3/1991 Bieniarz et al. ............ 435/176

FOREIGN PATENT DOCUMENTS

| GB | 2236185 A | 3/1991 |
| GB | 2236185 B | 3/1994 |
| WO | WO 94/04557 A1 | 3/1994 |
| WO | WO 94/28418 A1 | 12/1994 |

OTHER PUBLICATIONS

Hutchens et all (FEBS, vol. 296, No. 1, pp. 99–102, Jan. 1992).*
Carr et al (Analytical Biochemistry 157, 396–406, 1986).*
Tang et al (Rapid Communication in Mass Spectrometry, vol. 6, pp. 365–368, 1992).*
Hillenkamp et al., "Matrix–Assisted Laser Desorption/Ionization Mass Spectrometry of Biopolymers," *Analytical Chemistry*, 83(24):1193–1203 (1991).
Nakanishi et al., "Laser Desorption Time–of–flight Mass Spectrometric Analysis of Transferrin Precipitated with Antiserum: A Unique Simple Method to Identify Molecular Weight Variants," *Biological Mass Spectrometry*, 23:230–233 (1994).
The Nobel Prize in Chemistry, Oct. 9, 2002, 8 pages, http://nobelprize.org/nobel_prizes/chemistry/laureates/2002/public.html.

* cited by examiner

*Primary Examiner*—Padmashri Ponnaluri

(57) ABSTRACT

This invention relates generally to methods and apparatus for desorption and ionization of analytes for the purpose of subsequent scientific analysis by such methods, for example, as mass spectrometry or biosensors. More specifically, this invention relates to the field of mass spectrometry, especially to the type of matrix-assisted laser desorption/ionization, time-of-flight mass spectrometry used to analyze macromolecules, such as proteins or biomolecules. Most specifically, this invention relates to the sample probe geometry, sample probe composition, and sample probe surface chemistries that enable the selective capture and desorption of analytes, including intact macromolecules, directly from the probe surface into gas (vapor) phase without added chemical matrix.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 8–20 is confirmed.

Claim 1 is determined to be patentable as amended.

Claims 2–7, dependent on an amended claim, are determined to be patentable.

1. A method for detecting an analyte comprising the steps of:
   (a) capturing the analyte from a sample on a sample presenting surface of a mass spectrometer probe, wherein the surface is derivatized with an affinity reagent that binds the analyte, wherein the affinity reagent is immobilized by covalent bonding to the sample presenting surface;
   (b) applying matrix to the analyte on the sample presenting surface; and [(a)]
   (*c*) detecting the captured analyte by laser desorption/ionization mass spectrometry without substantial destruction of the analyte by the laser.

* * * * *